US008767307B2

(12) United States Patent
Nakamura et al.

(10) Patent No.: US 8,767,307 B2
(45) Date of Patent: Jul. 1, 2014

(54) OBJECTIVE OPTICAL SYSTEM

(71) Applicant: Olympus Medical Systems Corp., Tokyo (JP)

(72) Inventors: Minoru Nakamura, Tokyo (JP); Yasuaki Ushio, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/109,015

(22) Filed: Dec. 17, 2013

(65) Prior Publication Data

US 2014/0104707 A1 Apr. 17, 2014

Related U.S. Application Data

(63) Continuation of application No. PCT/JP2012/065704, filed on Jun. 20, 2012.

(30) Foreign Application Priority Data

Jun. 24, 2011 (JP) ................. 2011-140280
Jun. 24, 2011 (JP) ................. 2011-140281
Jun. 24, 2011 (JP) ................. 2011-140282

(51) Int. Cl.
  *G02B 21/02* (2006.01)
  *G02B 9/34* (2006.01)
  *G02B 23/24* (2006.01)
  *G02B 13/00* (2006.01)
  *A61B 1/00* (2006.01)

(52) U.S. Cl.
  CPC ............ *G02B 23/243* (2013.01); *G02B 13/006* (2013.01); *A61B 1/00163* (2013.01)
  USPC .......................................... 359/660; 359/772

(58) Field of Classification Search
  CPC ............ G02B 23/243; G02B 23/2407; G02B 13/006; G02B 13/004; G02B 9/34; A61B 1/00163
  USPC ................... 359/660, 714, 771, 772
  See application file for complete search history.

(56) References Cited

U.S. PATENT DOCUMENTS 5,216,545 A * 6/1993 Saito ............................. 359/661
6,441,966 B2 * 8/2002 Kajitani ....................... 359/660
(Continued)

FOREIGN PATENT DOCUMENTS

JP       06-222265        8/1994
JP       08-076010        3/1996
(Continued)

OTHER PUBLICATIONS

International Search Report, dated Sep. 25, 2012, issued in corresponding International Application No. PCT/JP2012/065704.

*Primary Examiner* — David N Spector
(74) *Attorney, Agent, or Firm* — Kenyon & Kenyon LLP

(57) ABSTRACT

Provided is an objective optical system comprising, in order from an object side: an aperture stop; a positive first group; a second group; a positive third group; and a fourth group, wherein the first group is formed of a single meniscus lens or plano-convex lens, whose convex surface faces an image side, the second group is formed of a single lens, the third group is formed of a cemented lens consisting of a positive lens and a negative lens, the fourth group is formed of a single lens, and Conditional Expressions (7) and (8) below are satisfied, where f is a focal length of an entire system, f4 is a focal length of the fourth group, and f2 is a focal length of the second group.

$$-0.5 < f/f4 < -0.001 \quad (7)$$

$$0.1 \leq |f4/f2| \leq 5. \quad (8)$$

4 Claims, 31 Drawing Sheets

(56) References Cited

U.S. PATENT DOCUMENTS

| | | | |
|---|---|---|---|
| 6,914,728 B2 * | 7/2005 | Sharma | 359/660 |
| 2014/0018628 A1 * | 1/2014 | Kanazawa et al. | 600/176 |

FOREIGN PATENT DOCUMENTS

| | | |
|---|---|---|
| JP | 10-090596 | 4/1998 |
| JP | 10-197806 | 7/1998 |
| JP | 2001-318310 | 11/2001 |
| JP | 2002-162561 | 6/2002 |
| JP | 2004-251958 | 9/2004 |
| JP | 2004-325713 | 11/2004 |
| JP | 2005-091464 | 4/2005 |
| JP | 2005-326682 | 11/2005 |
| JP | 2006-293042 | 10/2006 |
| JP | 2009-223183 | 10/2009 |
| JP | 2009-251227 | 10/2009 |
| JP | 2011-017918 | 1/2011 |
| WO | WO 2008/032447 | 3/2008 |

* cited by examiner

OBJECTIVE OPTICAL SYSTEM

CROSS-REFERENCE TO RELATED APPLICATIONS

This is a continuation of International Application PCT/JP2012/065704, with an international filing date of Jun. 20, 2012, which is hereby incorporated by reference herein in its entirety. This application claims the benefit of Japanese Patent Applications No. 2011-140280, No. 2011-140281 and No. 2011-140282, the contents of which are incorporated herein by reference.

TECHNICAL FIELD

The present invention relates to a small wide-angle objective optical system that is used in an endoscope, a camera-equipped cellular phone, and so forth.

BACKGROUND ART

In recent years, there have been advances toward high-definition, high-pixel-count solid-state imaging devices, such as CCDs, CMOS sensors, and so forth, and there is also a demand for achieving an increased image-capturing area, that is, a wider viewing angle. On the other hand, there is a high demand for achieving a size reduction of imaging optical systems from the viewpoint of portability and mobility. In particular, with imaging optical systems designed for an endoscope, it is necessary to achieve a size reduction, a cost reduction, and a wider viewing angle at the same time as achieving high definition, and thus, there is a demand for an objective optical system having a wide-angle configuration in which aberrations are also suppressed with a small number of lenses.

Conventional objective optical systems designed for an endoscope generally have a retrofocus-type four- to six-lens configuration (for example, see Patent Literature 1) or a two- to four-lens configuration (for example, see Patent Literatures 2, 3, and 5). In addition, there are known systems that are designed for digital cameras and camera-equipped cellular phones, having a three-lens configuration, referred to as triplet (for example, see Patent Literature 4), or a four-group configuration (for example, see Patent Literature 6).

CITATION LIST

Patent Literature

{PTL 1} Japanese Unexamined Patent Application, Publication No. 2009-223183
{PTL 2} Japanese Unexamined Patent Application, Publication No. 2009-251227
{PTL 3} Japanese Unexamined Patent Application, Publication No. 2011-17918
{PTL 4} Japanese Unexamined Patent Application, Publication No. 2004-325713
{PTL 5} Japanese Unexamined Patent Application, Publication No. 2002-162561
{PTL 6} Japanese Unexamined Patent Application, Publication No. 2006-293042
{PTL 7} Japanese Unexamined Patent Application, Publication No. Hei 10-197806
{PTL 8} PCT International Publication No. WO2008/032447

SUMMARY OF INVENTION

The present invention provides an objective optical system comprising, in order from an object side an aperture stop; a positive first group; a second group; a positive third group; and a fourth group, wherein the first group is formed of a single meniscus lens or plano-convex lens, whose convex surface faces an image side, the second group is formed of a single lens, the third group is formed of a cemented lens consisting of a positive lens and a negative lens, the fourth group is formed of a single lens, and Conditional Expressions (7) and (8) below are satisfied:

$$-0.5 < f/f4 < -0.001, \text{ and} \quad (7)$$

$$0.1 \le |f4/f2| \le 5, \quad (8)$$

where f is a focal length of an entire system, f4 is a focal length of the fourth group, and f2 is a focal length of the second group.

DESCRIPTION OF EMBODIMENTS

An objective optical system according to the present invention will be described in detail below by means of first to third embodiments and Examples.

In aberration diagrams for each Example, (a) shows vertical spherical aberration, (b) shows astigmatism, (c) shows magnification chromatic aberration, (d) is distortion (unit, %), and (e) shows vertical comatic aberration (image height ratio of 0.8). In addition, in the diagram (b) for astigmatism, the solid line indicates the sagittal image plane (s), and the broken line indicates the meridional image plane (m).

In addition, in lens data described in the respective Examples, r is the radius of curvature, d is the surface spacing, ne is the refractive index with respect to the e line, vd is the Abbe number with respect to the d line, ER is the effective radius of the lens surface, OBJ is an object plane, and IMG is an image plane. A surface corresponding to an aperture stop is indicated by S beside the surface number. An aspheric surface is indicated by * beside the surface number, and the paraxial radius of curvature r of an aspheric-surface shape, a cone constant K, and an aspheric surface coefficient Ai (i=2, 4, 6, or 8) that are expressed in the following Expression are included in Aspheric Surface Data. In the following Expression, the direction of the optical axis is z, and a direction perpendicular to the optical axis is y. However, when the value of the aspheric surface coefficient Ai is zero, the description thereof will be omitted in the Aspheric Surface Data of the respective Examples.

$$z=(y^2/r)/[1+\{1-(1+K)(y/r)^2\}^{1/2}]+A2y^2+A4y^4+A6y^6+A8y^8$$

First Embodiment

An objective optical system 1 according to a first embodiment will be described below with reference to FIG. 1.

Figure 1:
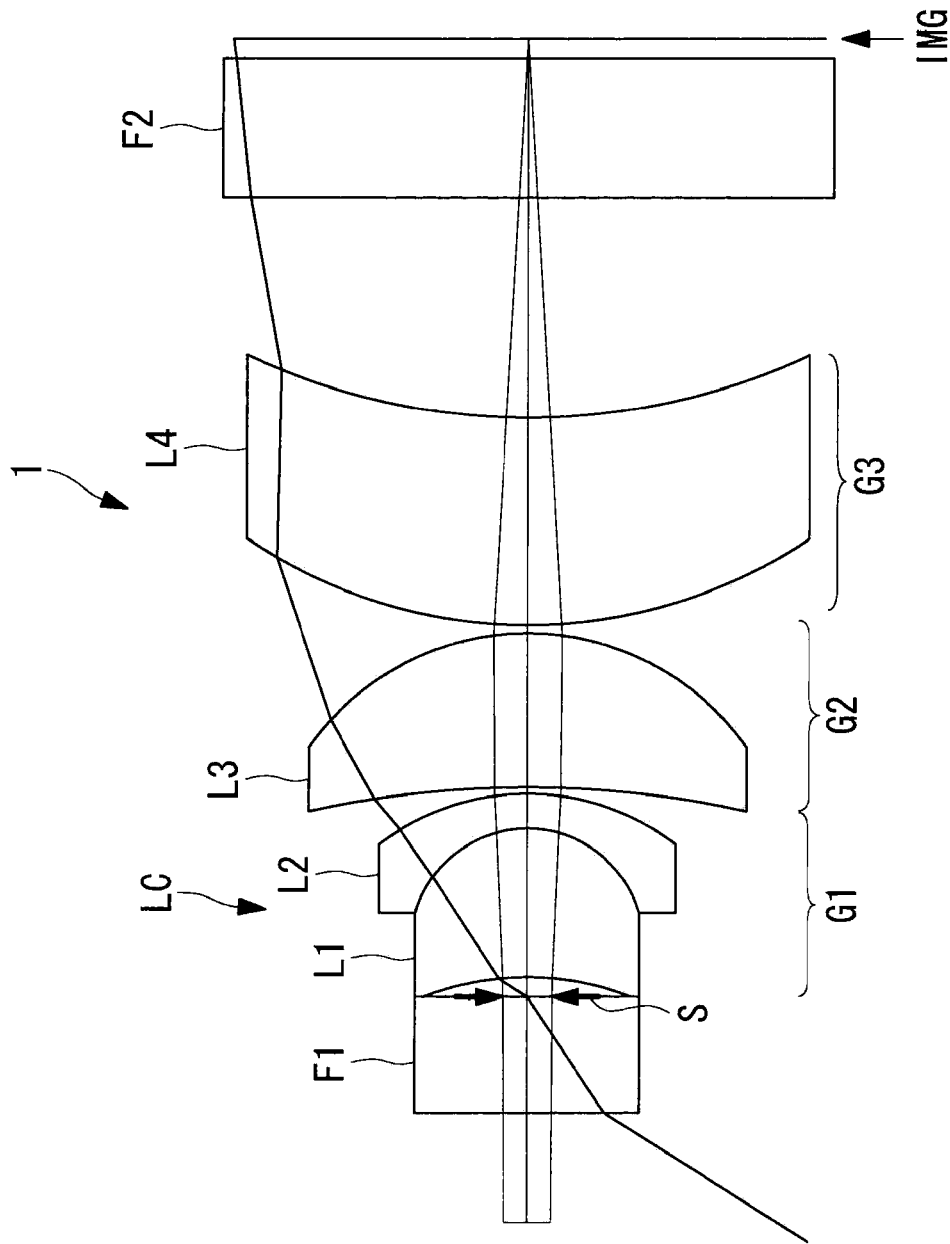
FIG. 1 is a diagram showing the overall configuration of an objective optical system according to a first embodiment.

The objective optical system 1 according to this embodiment is a wide-angle objective optical system having an angle of view equal to or greater than 60° and is formed of, in order from the object side, an aperture stop S, a positive first group G1, a positive second group G2, and a third group G3, as shown in FIG. 1. Reference signs F1 and F2 indicate flat-parallel plates. In addition, an arrow IMG indicates an image plane.

The first group G1 is formed of a cemented lens LC including a positive lens L1 and a negative lens L2. In the cemented lens LC, an object-side surface of the positive lens L1, which is a surface closest to the object side, is a concave surface toward the object side, and an image-side surface of the negative lens L2, which is a surface closest to the image side, is a convex surface toward the image side.

The second group G2 is formed of a single positive meniscus lens L3 whose convex surface faces the image side.

The third group G3 is formed of a single meniscus lens L4 whose convex surface faces the object side.

The objective optical system 1 satisfies Conditional Expressions (1) to (5) below:

$$0.001 \leq |f/f3| \leq 0.3, \quad (1)$$

$$2 < |(Ca+Cb)/(Ca-Cb)| < 50, \quad (2)$$

$$0.2 < f/f1 < 0.7, \quad (3)$$

$$-9 < (C1+C3)/(C1-C3) < -4, \text{ and} \quad (4)$$

$$0.3 < f/f2 < 0.8, \quad (5)$$

where f is the focal length of the entire system, f1 is the focal length of the first group G1, f2 is the focal length of the second group G2, f3 is the focal length of the third group G3, C1 is the curvature of the object-side surface of the positive lens L1, C3 is the curvature of the image-side surface of the negative lens L2, Ca is the curvature of the object-side surface of the meniscus lens L4, and Cb is the curvature of the image-side surface of the meniscus lens L4.

As described in Patent Literature 3, in order to reduce the size of the objective optical system, it is effective to employ a configuration in which the aperture is disposed on the object side, and in which a positive first group and a positive second group are included. However, with this configuration, it is not possible to sufficiently suppress the off-axis aberrations when the angle of view is set to have a wide viewing angle, and thus, it is difficult to ensure high enough performance to be compatible with a high-definition imaging device. Therefore, with the aspect, by employing the configuration including, in order from the object side, the aperture stop, the positive first group, the positive second group, and the third group, it is possible to satisfactorily correct off-axis aberrations (comatic aberration, astigmatic difference, and field curvature) and to suppress the occurrence thereof even with a wide angle of view. In particular, it is possible to keep the Petzval sum low due to the power distribution of the three-group configuration.

In addition, with the configuration of the above-described aspect, it is possible to gradually increase the distance between an off-axis beam and the center optical axis toward the image side from the aperture stop disposed closest to the object side. Therefore, it is possible to correct the comatic aberration occurring in the first group at the second group and the third group while keeping the influences on the on-axis performance, the focal length, and the overall length low.

In addition, in order to ensure high enough performance to be compatible with a high-definition imaging device while achieving a wide viewing angle, it is necessary to sufficiently suppress magnification chromatic aberration. In Patent Literature 3, although the magnification chromatic aberration is corrected by a cemented lens disposed on the image side, the size of the cemented lens in this arrangement becomes about the same as the size of the imaging device. Because doing so increases the power of the convex lens due to the nature of the cemented lens, the center thereof becomes thicker to ensure a sufficient edge thickness at the lens edge, and thus, it is necessary to increase the overall size together with the outer diameter. Furthermore, because the radius of curvature at a joining surface becomes small relative to the outer diameter, it is necessary to use a negative lens having a deep concave surface, which deteriorates the processability. In contrast, with the aspect, the size of the cemented lens can be reduced by disposing the cemented lens in the first group where the lens outer diameter can be minimized, and thus, it is also possible to achieve satisfactory processability.

In addition, in the first group, the surface closest to the object side is a concave surface toward the object side, the surface closest to the image side is a convex surface toward the image side, and thus, the principal point of the first group is moved away from the aperture stop toward the image side. By doing so, the power arrangement of the first group becomes substantially concentric with respect to the aperture stop, which makes it possible to suppress the occurrence of an astigmatic difference and off-axis comatic aberration.

In addition, by setting the power of the third group within an appropriate range in accordance with Conditional Expression (1), it is possible to satisfactorily correct aberrations. When $|f/f3|$ exceeds the upper limit of 0.3, because the relative power of the third group becomes too high, the off-axis image plane becomes inclined due to overcorrection of the Petzval sum and the comatic aberration is increased, which decrease the image quality. On the other hand, when $|f/f3|$ is less than the lower limit of 0.001, because the power of the third group becomes relatively low and the power of the first group becomes relatively high, high comatic aberration occurs in the first group or the field curvature cannot sufficiently be corrected, which decreases the image quality.

In the above-described aspect, it is preferable that the third group be formed of a meniscus lens whose convex surface faces the object side.

With the third group, the field curvature is adjusted by correcting the Petzval sum, and the comatic aberration occurring in the first group is corrected. With the third group, the object-side surface thereof is convex toward the object side, thus making it possible to satisfactorily correct the comatic aberration, and also, the image-side surface is concave toward the image side, which makes it possible to satisfactorily correct the field curvature.

In the above-described aspect, it is preferable that the third group satisfy Conditional Expression (2).

When $|(Ca+Cb)/(Ca-Cb)|$ is equal to or less than the lower limit of 2, the shape of the meniscus lens approaches that of a double-convex lens or a double-concave lens, and thus, it is difficult to correct the comatic aberration. On the other hand, when $|(Ca+Cb)/(Ca-Cb)|$ is equal to or greater than the upper limit of 50, the meniscus lens becomes thick because the amount of protrusion of the convex surface thereof increases. In addition, it is difficult to ensure a sufficient edge thickness of the lens edge.

In the configuration that satisfies the above-described Conditional Expression (2), it is preferable that the first group satisfy Conditional Expression (3).

In Conditional Expression (3), when f/f1 is equal to or less than the lower limit of 0.2, the power of the second group and that of the third group become relatively high, which causes the off-axis performance to deteriorate. On the other hand, when f/f1 is equal to or greater than the upper limit of 0.7, the power of the first group becomes relatively high, which increases the occurrence of comatic aberration, and thus, it is difficult to sufficiently correct the comatic aberration in the second group and the third group.

In the configuration that satisfies the above-described Conditional Expression (3), it is preferable that the first group satisfy Conditional Expression (4).

In Conditional Expression (4), when $(C1+C3)/(C1-C3)$ is equal to or less than the lower limit of −9, the meniscus lens becomes thick because the amount of protrusion of the convex surface thereof increases. In addition, it is difficult to ensure a sufficient edge thickness of the lens edge. On the other hand, when $(C1+C3)/(C1-C3)$ is equal to or greater than the upper limit of −4, the shape of the meniscus lens approaches that of a plano-convex lens. In this case, because the curvature thereof deviates from the concentric state with respect to the aperture stop, an astigmatic difference increases, which causes the off-axis performance to deteriorate.

Furthermore, in the configuration that satisfies the above-described Conditional Expression (3), it is preferable that the second group satisfy Conditional Expression (5).

In Conditional Expression (5), when f/f2 is equal to or less than the lower limit of 0.3, the power of the first group and that of the third group become relatively high, which causes the off-axis performance to deteriorate. On the other hand, when f/f2 is equal to or greater than the upper limit of 0.8, the power of the second group becomes relatively high, which increases the occurrence of comatic aberration, and thus, it is difficult to sufficiently correct the comatic aberration in the third group.

In the configuration that satisfies the above-described Conditional Expression (5), the second group may be formed of, in order from the object side, a positive meniscus lens whose convex surface faces the image side and a positive lens in which an image-side surface thereof is a convex surface toward the image side.

Because the first group is a positive cemented lens, it is difficult to increase the power thereof, and thus, it is necessary to increase the power of the second group. Therefore, the occurrence of aberration can be prevented by dividing the second group into two positive lenses. In addition, by employing a positive meniscus lens whose convex surface faces the image side as the lens on the object side and by setting the lens on the image side so that the image-side surface thereof is convex toward the image side, the curvatures thereof become substantially concentric with respect to the aperture, which makes it possible to suppress the occurrence of an astigmatic difference.

Although having a small size and a wide viewing angle, the thus-configured objective optical system 1 according to this embodiment satisfactorily corrects aberration, and therefore, the objective optical system 1 is also suitably compatible with a high-definition, high-pixel-count solid-state imaging device.

Note that, in this embodiment, although the second group G2 is formed of the single positive meniscus lens L3, alternatively, the second group G2 may be formed of, in order from the object side, a positive meniscus lens whose convex surface faces the image side and a positive lens in which the image-side surface thereof is a convex surface toward the image side. In this configuration, it is preferable that the second group G2 satisfy Conditional Expression (6) below:

$$-4 \leq f3/f21 \leq -0.5, \qquad (6)$$

where f21 is the focal length of the positive meniscus lens, and f3 is the focal length of the third group G3.

In the second group, the field curvature and the comatic aberration occur in the object-side positive lens, and these aberrations are corrected at the third group. Therefore, in Conditional Expression (6), when f3/f21 is less than the lower limit of −4, the occurrence of aberrations increases in the object-side positive lens in the second group, which makes it difficult to sufficiently correct the aberrations at the third group. On the other hand, when f3/f21 is greater than the upper limit of −0.5, the image quality decreases due to the overcorrection of aberrations at the third group.

Examples of First Embodiment

Next, Examples 1 to 4 of the above-described first embodiment will be described with reference to FIGS. 2 to 9.

Example 1

Figure 2:
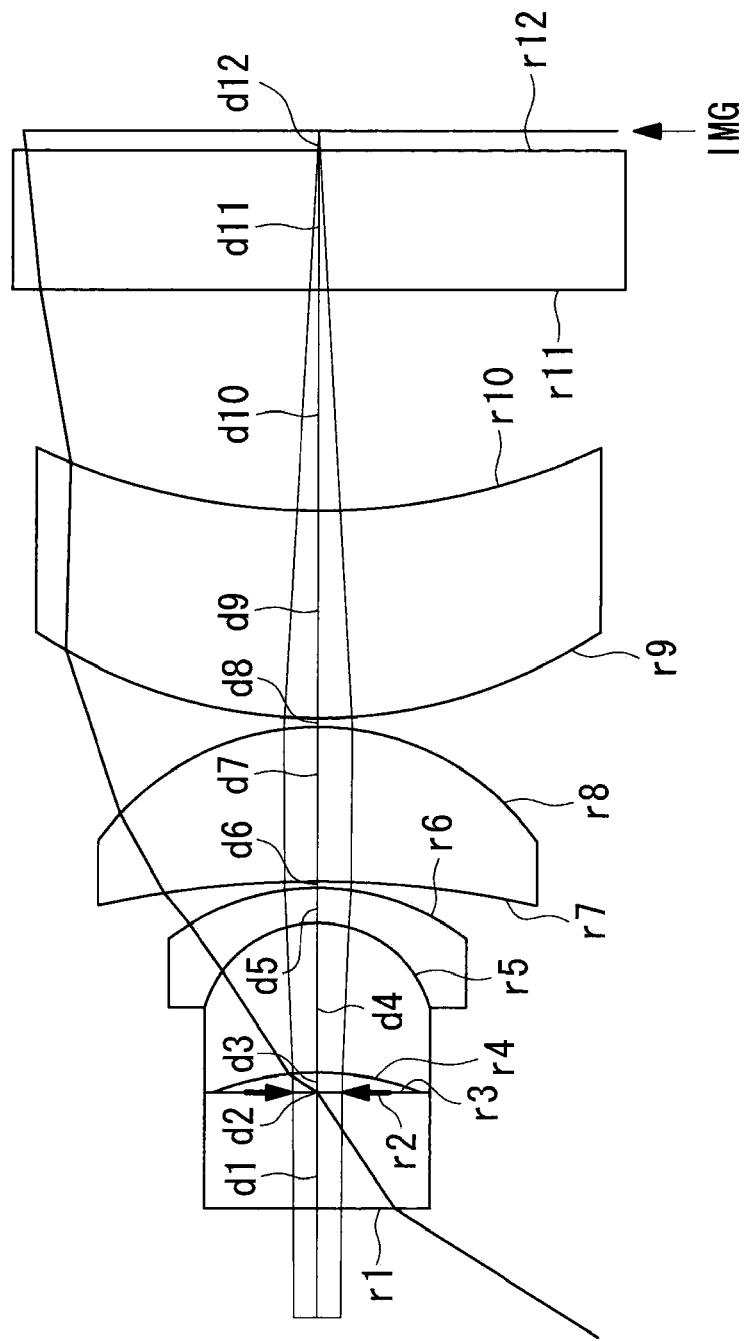
FIG. 2 is a cross-sectional view of a lens showing the overall configuration of the objective optical system according to Example 1 of the first embodiment.
Figure 3:
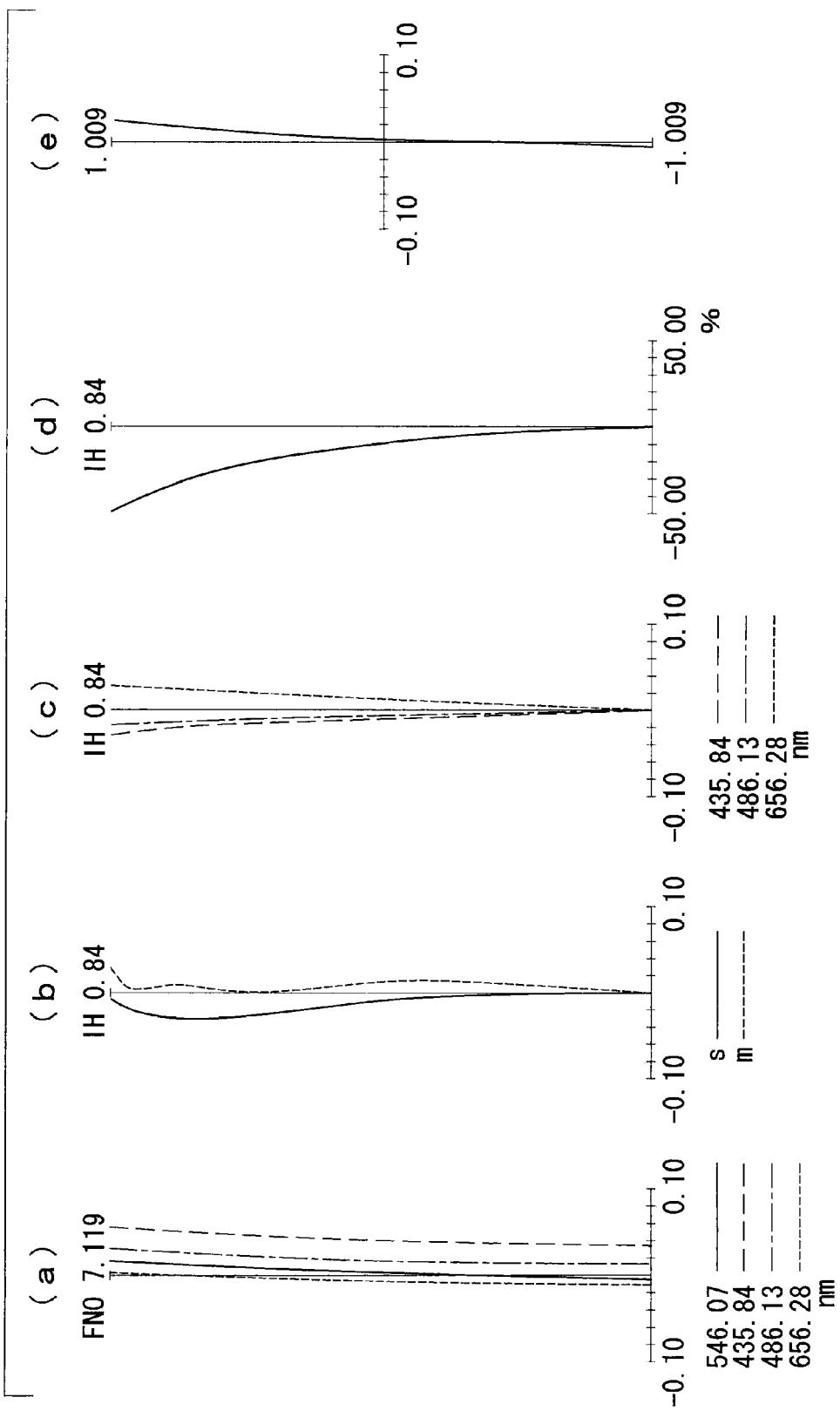
FIG. 3 is a diagram showing various types of aberration of the objective optical system in FIG. 2.

As shown in FIG. 2, in an objective optical system according to Example 1 of the first embodiment, the first group is formed of a cemented lens including two meniscus lenses, one positive and one negative; the second group is formed of a single positive meniscus lens whose convex surface faces the image side; and the third group is formed of a single meniscus lens whose convex surface faces the object side. FIG. 3 shows aberration diagrams of the thus-configured objective optical system of this Example.

Lens Data

| Surface Number | r | d | ne | vd | ER |
|---|---|---|---|---|---|
| OBJ | ∞ | 9.5782 | 1.00000 | | |
| 1 | ∞ | 0.3193 | 1.51825 | 64.14 | 0.286 |
| 2 | ∞ | 0.0000 | 1.00000 | | 0.070 |
| 3(S) | ∞ | 0.0536 | 1.00000 | | 0.070 |
| 4 | −0.8042 | 0.4182 | 1.72407 | 41.98 | 0.121 |
| 5 | −0.3297 | 0.0958 | 1.93429 | 18.90 | 0.284 |
| 6* | −0.6203 | 0.0192 | 1.00000 | | 0.389 |
| 7 | −2.8380 | 0.4241 | 1.53336 | 56.00 | 0.479 |
| 8* | −0.8494 | 0.0223 | 1.00000 | | 0.589 |
| 9* | 1.7704 | 0.5715 | 1.53336 | 56.00 | 0.766 |
| 10 | 1.8918 | 0.6089 | 1.00000 | | 0.737 |
| 11 | ∞ | 0.3831 | 1.51825 | 64.14 | 0.801 |
| 12 | ∞ | 0.0537 | 1.00000 | | 0.836 |
| IMG | ∞ | 0.0000 | | | |

Aspheric Surface Data

Surface 6

| r = −0.6203 | K = −0.4652 |
|---|---|
| A2 = 0.0000E+00 | A4 = 5.2561E−01 |
| A6 = −7.0139E−01 | A8 = 0.0000E+00 |

Surface 8

| r = −0.8494 | K = 0.2688 |
|---|---|
| A2 = 0.0000E+00 | A4 = −3.6881E−01 |
| A6 = 1.7365E−01 | A8 = 8.3006E−01 |

Surface 9

| r = 1.7704 | K = 0.3033 |
|---|---|
| A2 = 0.0000E+00 | A4 = 5.3091E−02 |
| A6 = 1.7766E−01 | A8 = −1.3199E−01 |

Miscellaneous data

| Focal length | 1.0 |
|---|---|
| Image height | 0.84 |
| Fno. | 7.119 |
| Effective Fno. | 7.420 |
| Distance to object point | 9.5782 |
| Half-angle of view | 58.3 |
| Distortion | −49.8% |

With the objective optical system according to this Example, the size thereof is small, having an overall length of about 3.5 times the image height, and an angle of view of 117° is also achieved. In addition, the power arrangement of the cemented lens in the first group and the selection of glasses are satisfactory, and thus, it is possible to satisfactorily correct the magnification chromatic aberration. Specifically, the value of the left side of the Expression below, which generally defines the achromatizing condition for a cemented lens, is −0.034, thus being sufficiently low and sufficiently satisfying the condition:

$$1/(f11 \times vd11) + 1/(f12 \times vd12) = 0,$$

where
f11 is the focal length of the positive meniscus lens in the first group,
vd11 is the Abbe number of the material for the positive meniscus lens in the first group,
f12 is the focal length of the negative meniscus lens in the first group, and
vd12 is the Abbe number of the material for the negative meniscus lens in the first group.

Example 2

Figure 4:
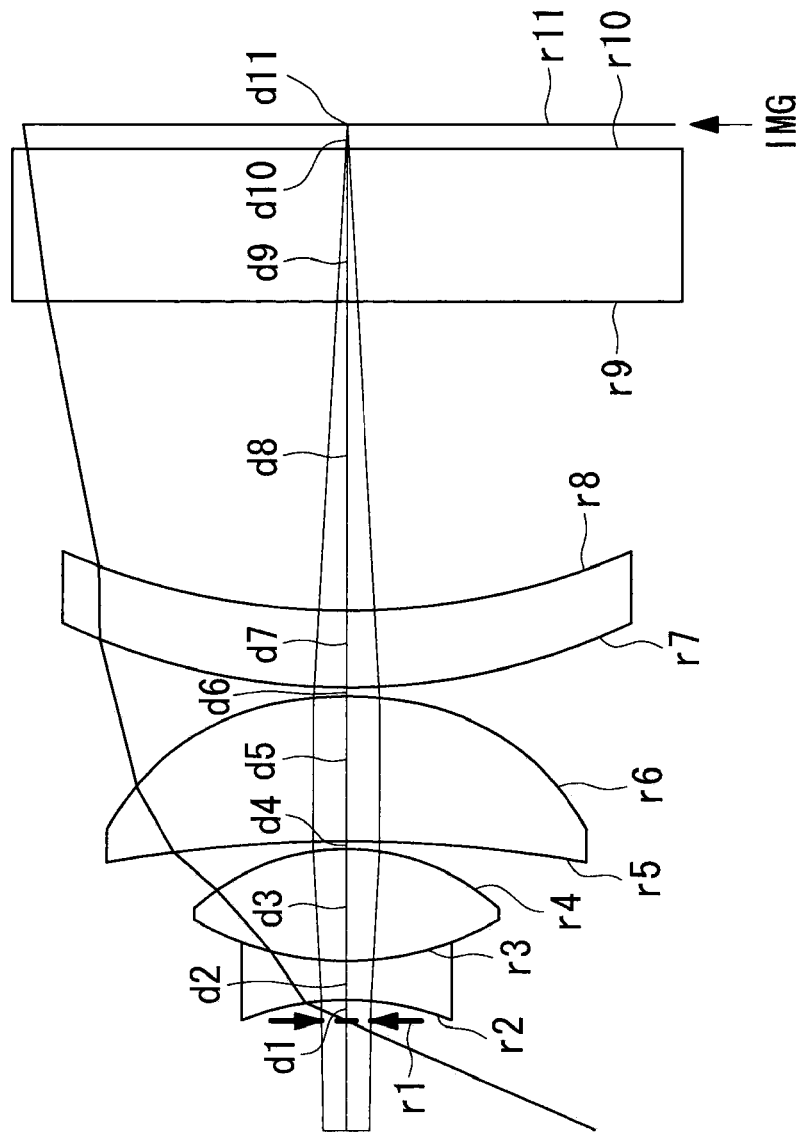
FIG. 4 is a cross-sectional view of a lens showing the overall configuration of the objective optical system according to Example 2 of the first embodiment.
Figure 5:
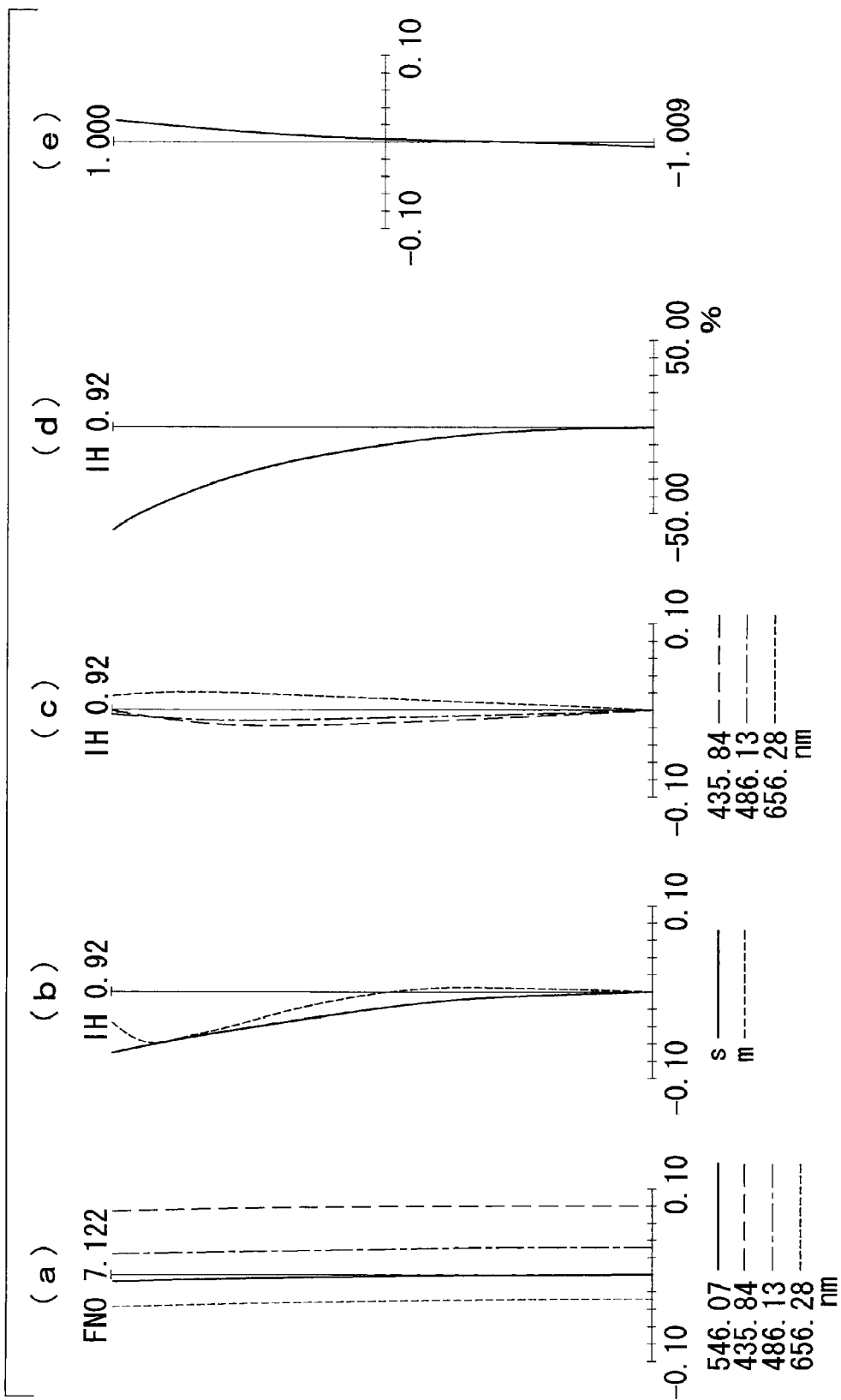
FIG. 5 is a diagram showing various types of aberration of the objective optical system in FIG. 4.

As shown in FIG. 4, in an objective optical system according to Example 2 of the first embodiment, the first group is formed of a cemented lens including a double-concave lens and a double-convex lens; the second group is formed of a single positive meniscus lens whose convex surface faces the image side; and the third group is formed of a single meniscus lens whose convex surface faces the object side. FIG. 5 shows aberration diagrams of the thus-configured objective optical system of this Example.

Lens Data

| Surface Number | r | d | ne | vd | ER |
|---|---|---|---|---|---|
| OBJ | ∞ | 10.5305 | 1.00000 | | |
| 1(S) | ∞ | 0.0590 | 1.00000 | | 0.070 |
| 2 | −0.7943 | 0.1053 | 1.93429 | 18.90 | 0.146 |
| 3 | 0.8644 | 0.3121 | 1.73234 | 54.68 | 0.261 |
| 4* | −0.5534 | 0.0211 | 1.00000 | | 0.398 |
| 5 | −3.7589 | 0.4001 | 1.73234 | 54.68 | 0.564 |
| 6* | −1.0547 | 0.0246 | 1.00000 | | 0.646 |
| 7* | 2.1599 | 0.2106 | 1.53336 | 56.00 | 0.772 |
| 8 | 2.0675 | 0.8497 | 1.00000 | | 0.764 |
| 9 | ∞ | 0.4212 | 1.51825 | 64.14 | 0.871 |
| 10 | ∞ | 0.0702 | 1.00000 | | 0.913 |
| 11 | ∞ | 0.0000 | 1.00000 | | 0.928 |
| IMG | ∞ | 0.0000 | | | |

-continued

Aspheric Surface Data

Surface 4

| | |
|---|---|
| r = −0.5534 | K = −0.4885 |
| A2 = 0.0000E+00 | A4 = 5.7879E−01 |
| A6 = −3.2845E−01 | A8 = 0.0000E+00 |

Surface 6

| | |
|---|---|
| r = −1.0547 | K = 0.2599 |
| A2 = 0.0000E+00 | A4 = −4.6661E−01 |
| A6 = 9.5445E−02 | A8 = −4.5977E−01 |

Surface 7

| | |
|---|---|
| r = 2.1599 | K = −0.1186 |
| A2 = 0.0000E+00 | A4 = 5.8487E−02 |
| A6 = −8.0494E−02 | A8 = 1.4847E−01 |

Miscellaneous data

| | |
|---|---|
| Focal length | 1.0 |
| Image height | 0.924 |
| Fno. | 7.122 |
| Effective Fno. | 7.412 |
| Distance to object point | 10.5305 |
| Half-angle of view | 66.2 |
| Distortion | −62.8% |

With the objective optical system according to this Example, the size thereof is small, having an overall length of about 2.7 times the image height, and an angle of view of 132° is also achieved. In addition, the power arrangement of the cemented lens in the first group and the selection of glasses are satisfactory, and thus, it is possible to satisfactorily correct the magnification chromatic aberration. Specifically, the value of the left side of the Expression below, which generally defines the achromatizing condition for a cemented lens, is −0.014, thus being sufficiently low and sufficiently satisfying the condition:

$$1/(f11 \times vd11) + 1/(f12 \times vd12) = 0,$$

where
f11 is the focal length of the double-concave lens in the first group,
vd11 is the Abbe number of the material for the double-concave lens in the first group,
f12 is the focal length of the double-convex lens in the first group, and
vd12 is the Abbe number of the material for the double-convex lens in the first group.

Example 3

Figure 6:
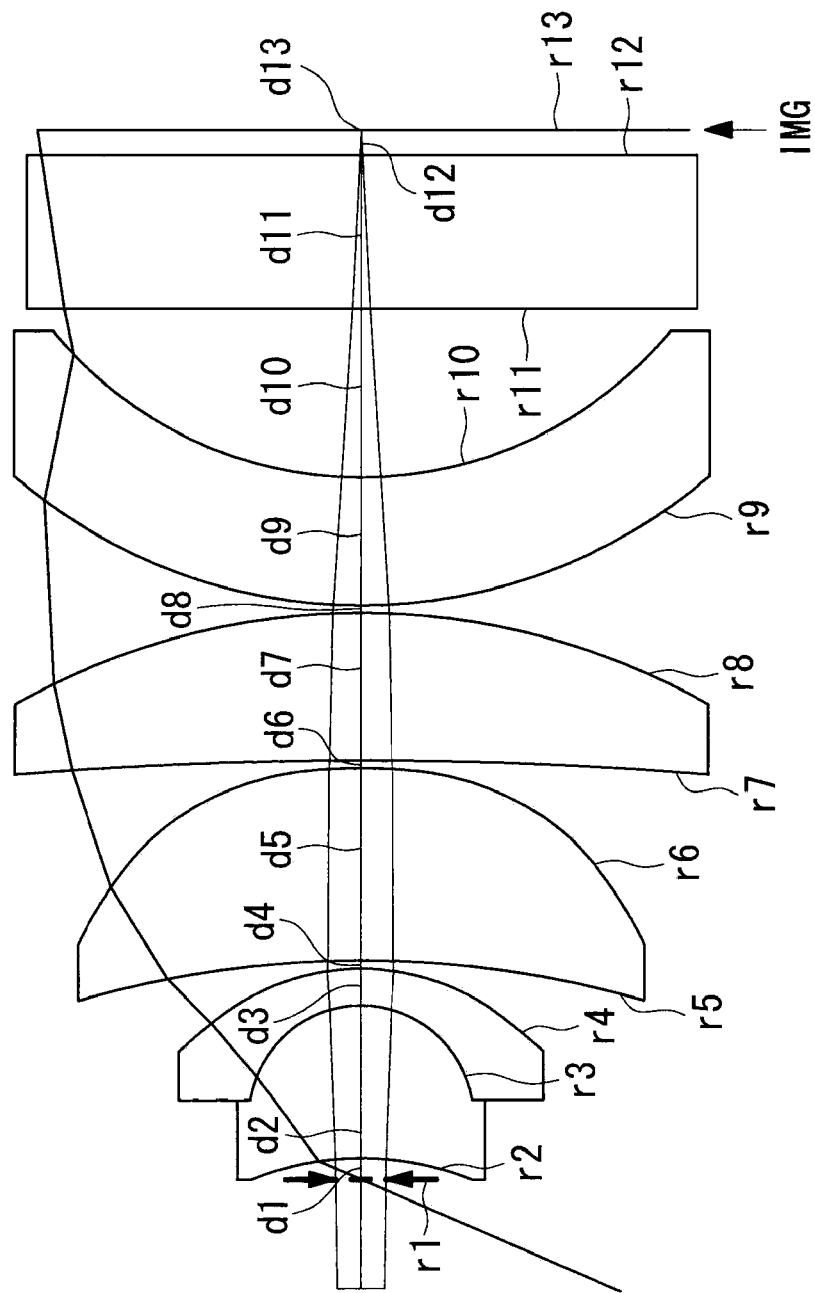
FIG. 6 is a cross-sectional view of a lens showing the overall configuration of the objective optical system according to Example 3 of the first embodiment.
Figure 7:
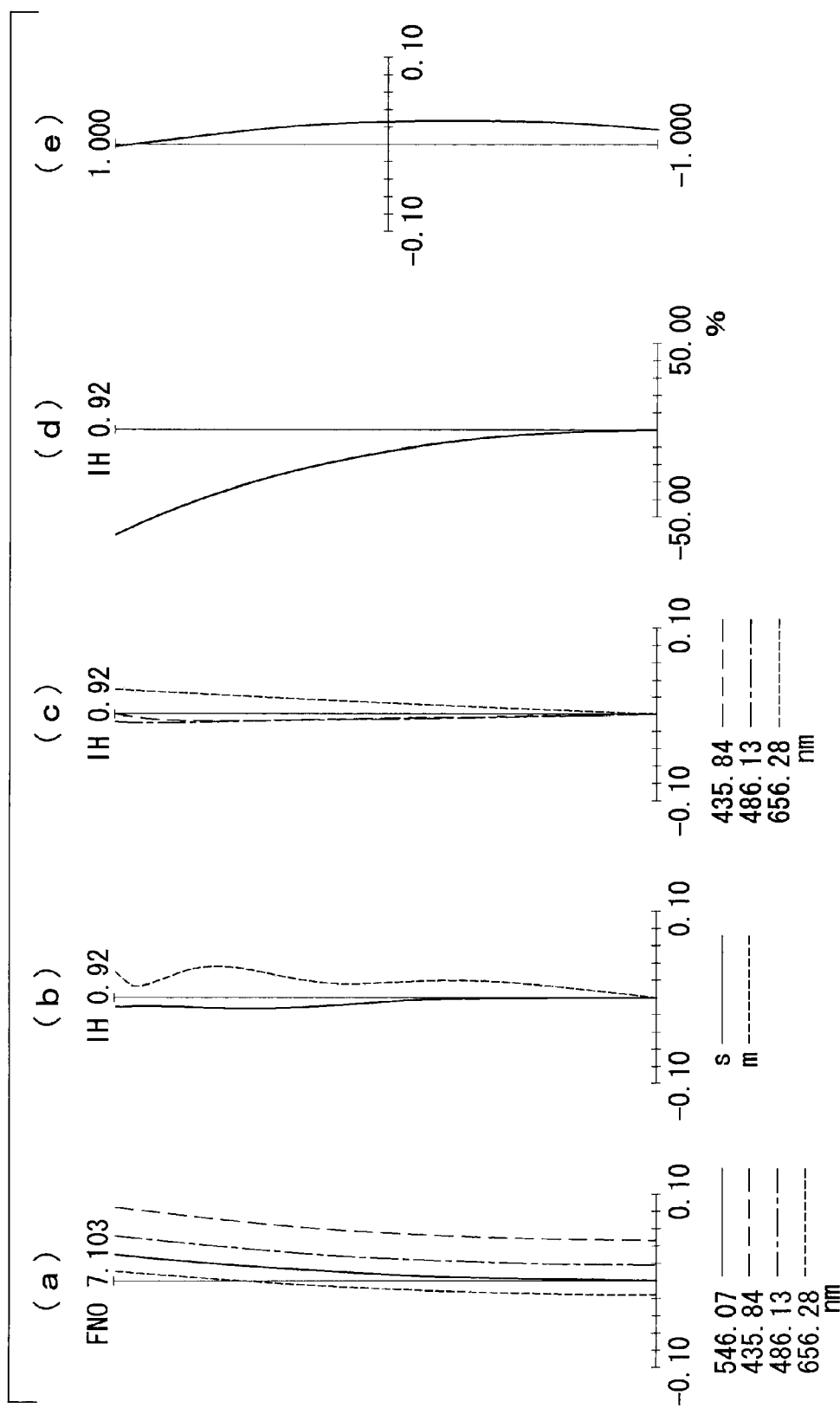
FIG. 7 is a diagram showing various types of aberration of the objective optical system in FIG. 6.

As shown in FIG. 6, in an objective optical system according to Example 3 of the first embodiment, the first group is formed of a cemented lens including two meniscus lenses, one positive and one negative; the second group is formed of two positive meniscus lenses whose convex surfaces face the image side; and the third group is formed of a single meniscus lens whose convex surface faces the object side. FIG. 7 shows aberration diagrams of the thus-configured objective optical system of this Example.

Lens Data

| Surface Number | r | d | ne | vd | ER |
|---|---|---|---|---|---|
| OBJ | ∞ | 10.5060 | 1.00000 | | |
| 1(S) | ∞ | 0.0588 | 1.00000 | | 0.070 |
| 2 | −0.8303 | 0.4203 | 1.73234 | 54.68 | 0.167 |
| 3 | −0.3175 | 0.1051 | 1.93429 | 18.90 | 0.313 |
| 4* | −0.5661 | 0.0210 | 1.00000 | | 0.480 |
| 5 | −2.9598 | 0.5293 | 1.53336 | 56.00 | 0.644 |
| 6* | −1.4920 | 0.0210 | 1.00000 | | 0.768 |
| 7 | −11.9054 | 0.4069 | 1.73234 | 54.68 | 0.902 |
| 8 | −2.0416 | 0.0210 | 1.00000 | | 0.948 |
| 9* | 1.6084 | 0.3502 | 1.53336 | 56.00 | 0.952 |
| 10 | 1.1460 | 0.4678 | 1.00000 | | 0.849 |
| 11 | ∞ | 0.4202 | 1.51825 | 64.14 | 0.864 |
| 12 | ∞ | 0.0700 | 1.00000 | | 0.912 |
| 13 | ∞ | 0.0000 | 1.00000 | | 0.924 |
| IMG | ∞ | 0.0000 | | | |

Aspheric Surface Data

Surface 4

| | |
|---|---|
| r = −0.5661 | K = −0.5030 |
| A2 = 0.0000E+00 | A4 = 7.1355E−01 |
| A6 = −9.1217E−01 | A8 = 0.0000E+00 |

Surface 6

| | |
|---|---|
| r = −1.4920 | K = 0.2997 |
| A2 = 0.0000E+00 | A4 = −7.2345E−01 |
| A6 = 6.7007E−01 | A8 = −7.3451E−01 |

Surface 9

| | |
|---|---|
| r = 1.6084 | K = 0.2571 |
| A2 = 0.0000E+00 | A4 = 4.7200E−03 |
| A6 = 2.5175E−03 | A8 = −3.3216E−03 |

Miscellaneous data

| | |
|---|---|
| Focal length | 1.0 |
| Image height | 0.922 |
| Fno. | 7.103 |
| Effective Fno. | 7.335 |
| Distance to object point | 10.506 |
| Half-angle of view | 66.5 |
| Distortion | −61.2% |

With the objective optical system according to this Example, the size thereof is small, having an overall length of about 3.1 times the image height, and an angle of view of 133° is also achieved. In addition, the power arrangement of the cemented lens in the first group and the selection of glasses are satisfactory, and thus, it is possible to satisfactorily correct the magnification chromatic aberration. Specifically, the value of the left side of the Expression below, which generally defines the achromatizing condition for a cemented lens, is −0.042, thus being sufficiently low and sufficiently satisfying the condition:

$$1/(f11 \times vd11) + 1/(f12 \times vd12) = 0,$$

where
f11 is the focal length of the positive meniscus lens in the first group,
vd11 is the Abbe number of the material for the positive meniscus lens in the first group,
f12 is the focal length of the negative meniscus lens in the first group, and
vd12 is the Abbe number of the material for the negative meniscus lens in the first group.

Example 4

Figure 8:
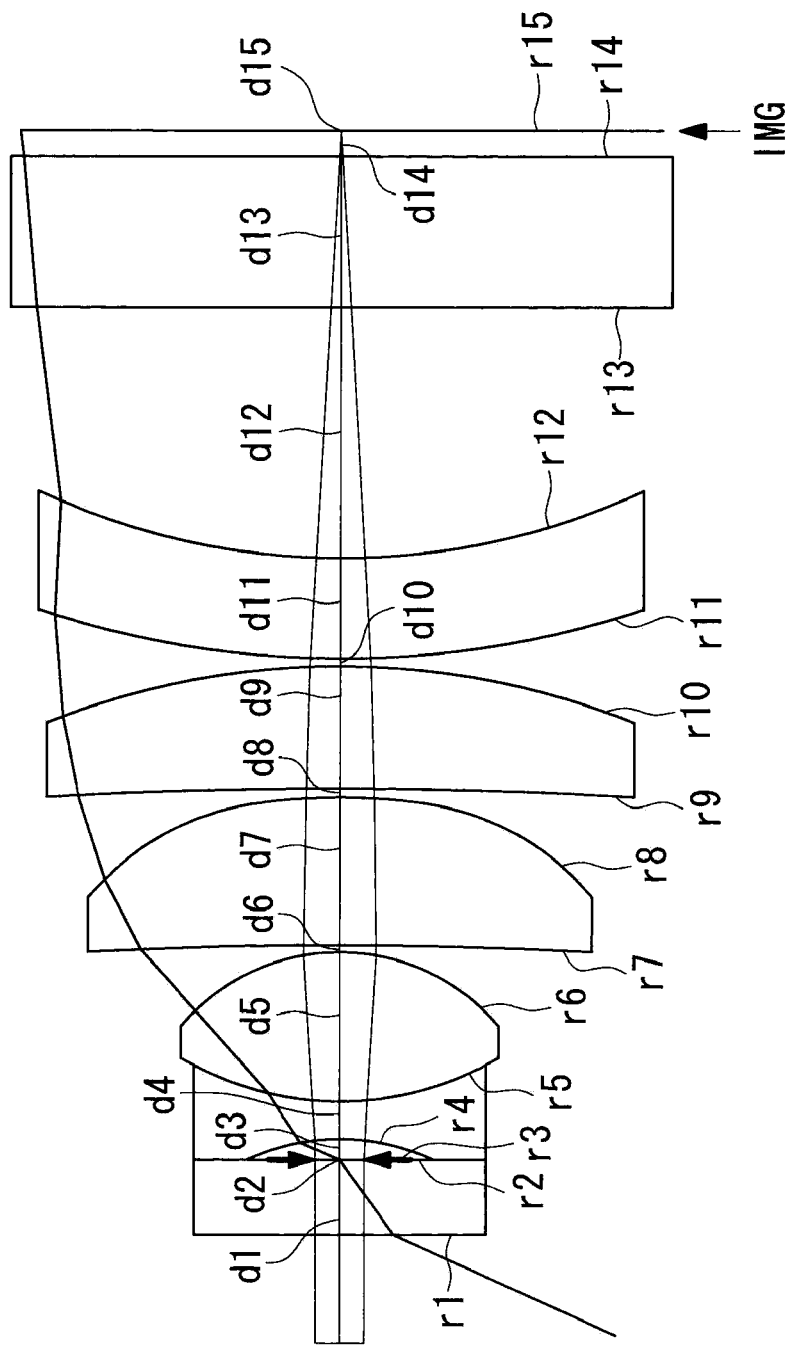
FIG. 8 is a cross-sectional view of a lens showing the overall configuration of the objective optical system according to Example 4 of the first embodiment.
Figure 9:
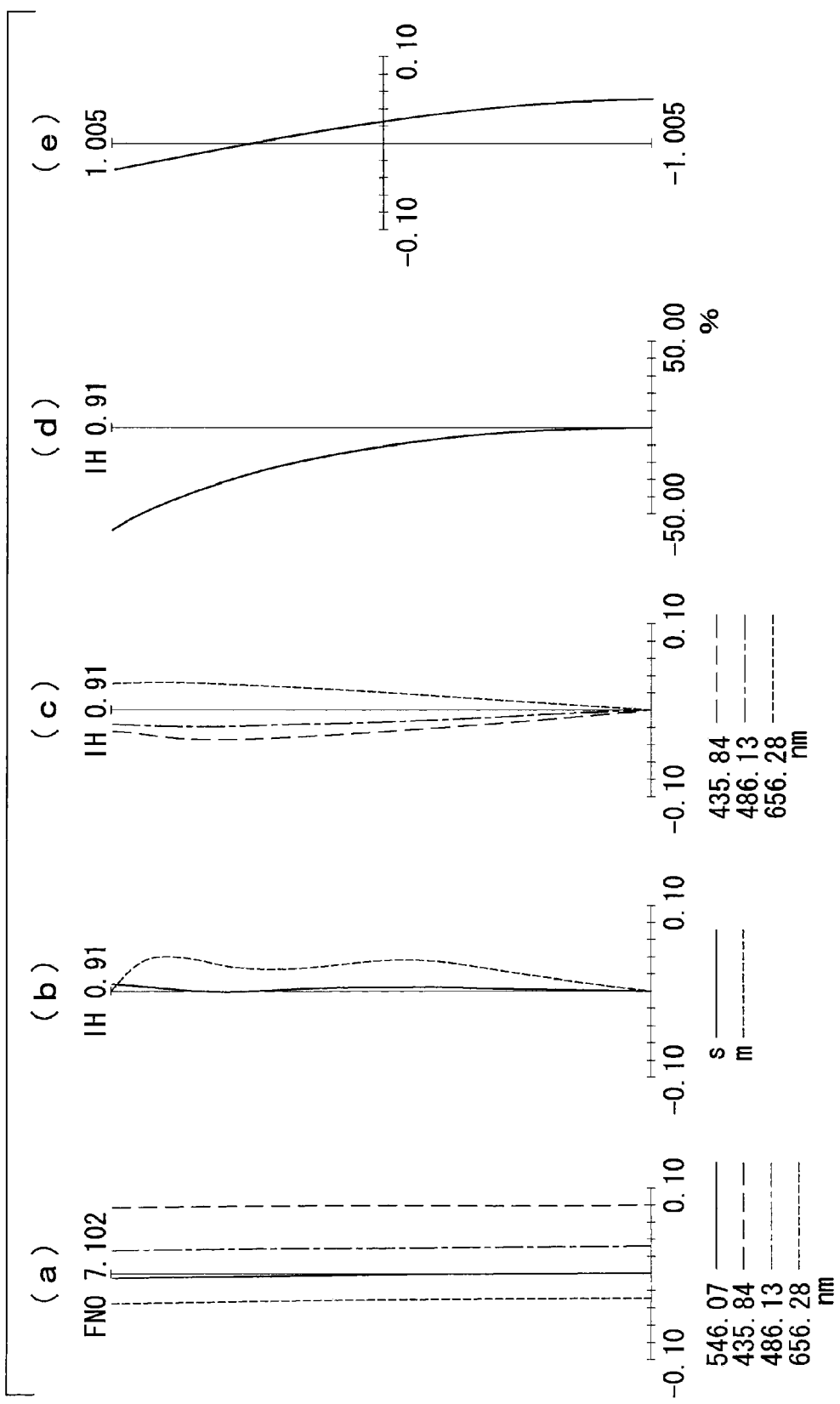
FIG. 9 is a diagram showing various types of aberration of the objective optical system in FIG. 8.

As shown in FIG. 8, in an objective optical system according to Example 4 of the first embodiment, the first group is formed of a cemented lens including a double-concave lens and a double-convex lens; the second group is formed of two positive meniscus lenses whose convex surfaces face the image side; and the third group is formed of a single meniscus lens whose convex surface faces the object side. FIG. 9 shows aberration diagrams of the thus-configured objective optical system of this Example.

Lens Data

| Surface Number | r | d | ne | vd | ER |
|---|---|---|---|---|---|
| OBJ | ∞ | 10.3535 | 1.00000 | | |
| 1 | ∞ | 0.2071 | 1.51825 | 64.14 | 0.380 |
| 2 | ∞ | 0.0000 | 1.00000 | | 0.070 |
| 3(S) | ∞ | 0.0580 | 1.00000 | | 0.070 |
| 4 | −0.7128 | 0.1035 | 1.93429 | 18.90 | 0.135 |
| 5 | 0.9212 | 0.4097 | 1.73234 | 54.68 | 0.380 |
| 6* | −0.5335 | 0.0207 | 1.00000 | | 0.414 |
| 7 | −11.8730 | 0.4086 | 1.53336 | 56.00 | 0.582 |
| 8* | −1.7600 | 0.0242 | 1.00000 | | 0.679 |
| 9 | −13.2586 | 0.3382 | 1.73234 | 54.68 | 0.756 |
| 10 | −2.2819 | 0.0207 | 1.00000 | | 0.800 |
| 11* | 3.6636 | 0.2761 | 1.53336 | 56.00 | 0.823 |
| 12 | 2.0883 | 0.6897 | 1.00000 | | 0.802 |
| 13 | ∞ | 0.4141 | 1.51825 | 64.14 | 0.867 |
| 14 | ∞ | 0.0690 | 1.00000 | | 0.900 |
| 15 | ∞ | 0.0000 | 1.00000 | | 0.908 |
| IMG | ∞ | 0.0000 | | | |

Aspheric Surface Data

Surface 6 r = −0.5335          K = −0.4108
A2 = 0.0000E+00   A4 = 4.7734E−01
A6 = −1.2498E+00  A8 = 0.0000E+00

Surface 8 r = −1.7600          K = 0.2745
A2 = 0.0000E+00   A4 = −5.5390E−01
A6 = 3.3596E−01   A8 = −3.9294E−01

Surface 11 r = 3.6636           K = 0.0838
A2 = 0.0000E+00   A4 = 1.1642E−01
A6 = −1.6562E−01  A8 = 1.1267E−01

Miscellaneous data

| Focal length | 1.0 |
|---|---|
| Image height | 0.908 |
| Fno. | 7.1022 |
| Effective Fno. | 7.339 |
| Distance to object point | 10.354 |
| Half-angle of view | 65.9 |
| Distortion | −60.5% |

With the objective optical system according to this Example, the size thereof is small, having an overall length of about 3.4 times the image height, and an angle of view of 132° is also achieved. In addition, the power arrangement of the cemented lens in the first group and the selection of glasses are satisfactory, and thus, it is possible to satisfactorily correct the magnification chromatic aberration. Specifically, the value of the left side of the Expression below, which generally defines the achromatizing condition for a cemented lens, is −0.013, thus being sufficiently low and sufficiently satisfying the condition:

$$1/(f11 \times vd11) + 1/(f12 \times vd12) = 0,$$

where
f11 is the focal length of the double-concave lens in the first group,
vd11 is the Abbe number of the material for the double-concave lens in the first group,
f12 is the focal length of the double-convex lens in the first group, and
vd12 is the Abbe number of the material for the double-convex lens in the first group.

Table 1 shows values of Conditional Expressions (1) to (6) for the objective optical systems according to Examples 1 to 4 of the first embodiment.

TABLE 1

| Conditional Expression | Example 1 | Example 2 | Example 3 | Example 4 |
|---|---|---|---|---|
| (1) | 0.051 | 0.00229 | 0.0985 | 0.103 |
| (2) | 30.180 | 5.595 | 5.958 | 3.651 |
| (3) | 0.283 | 0.323 | 0.498 | 0.426 |
| (4) | −7.744 | −5.595 | −5.285 | −6.950 |
| (5) | 0.473 | 0.531 | 0.503 | 0.516 |
| (6) | | | −2.025 | −2.538 |

Second Embodiment

Next, an objective optical system 1' according to a second embodiment of the present invention will be described with reference to FIG. 10.

Figure 10:
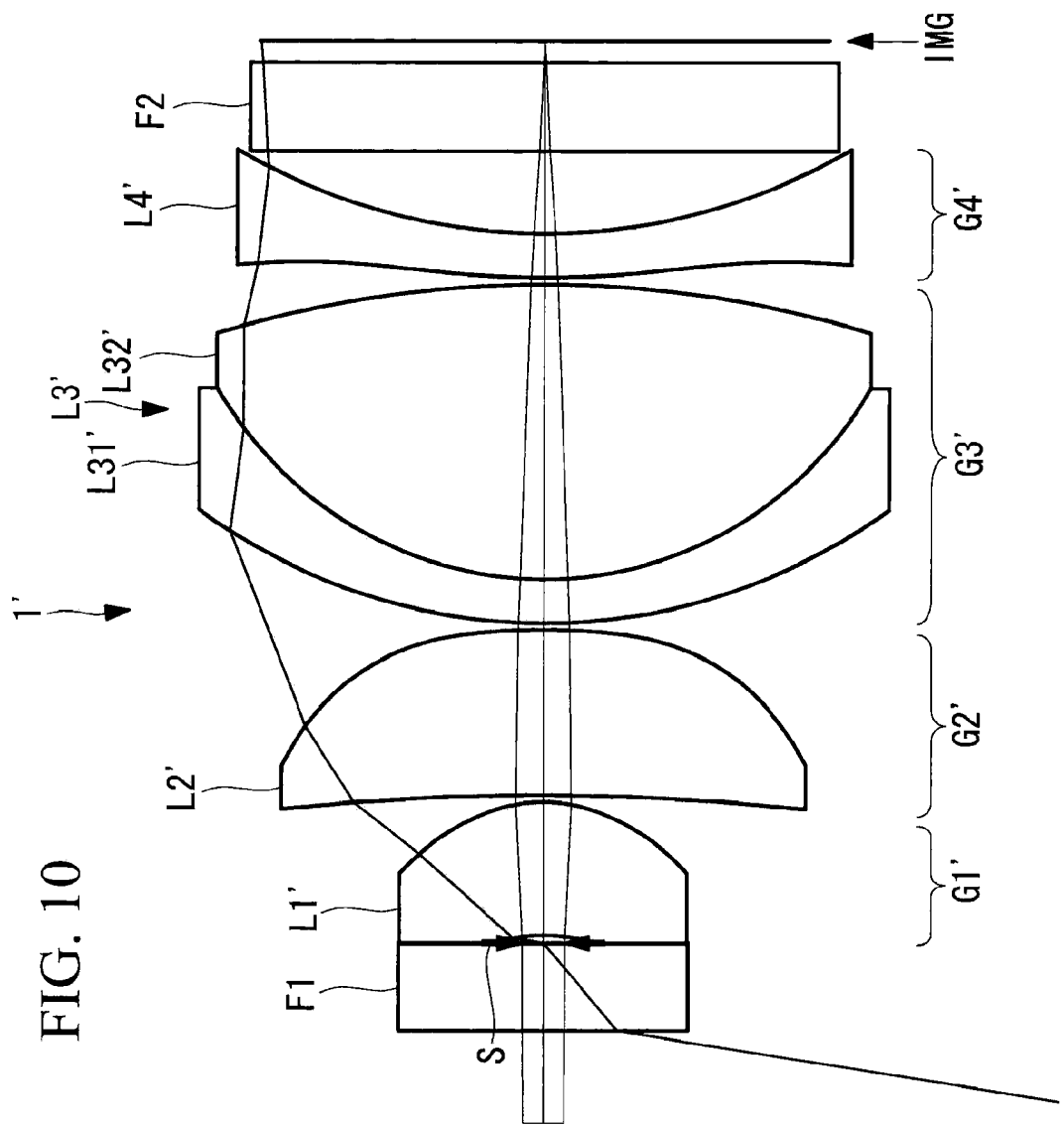
FIG. 10 is a diagram showing the overall configuration of an objective optical system according to a second embodiment of the present invention.

As shown in FIG. 10, an objective optical system 1' according to this embodiment is formed of, in order from the object side, an aperture stop S, a positive first group G1', a second group G2', a positive third group G3', and a fourth group G4'. Reference signs F1 and F2 indicate flat-parallel plates. In addition, an arrow IMG indicates an image plane.

The first group G1' is formed of a single meniscus lens L1' whose convex surface faces the image side.

The second group G2' is formed of a single meniscus lens L2' whose convex surface faces the image side.

The third group G3' is formed of a cemented lens in which a negative meniscus lens (negative lens) L31', whose convex surface faces the object side, and a double-convex lens (positive lens) L32' are attached to each other.

The fourth group G4' is formed of a single meniscus lens L4' whose convex surface faces the object side.

The objective optical system 1' satisfies Conditional Expressions (7) to (11) below:

$$-0.5 < f/f4 < -0.001, \quad (7)$$

$$0.1 \leq f4/f2 \leq 5, \quad (8)$$

$$0.3 < f/f3 < 0.8, \quad (9)$$

$$0.15 < f/f1 < 1.1, \text{ and} \quad (10)$$

$$1 \leq |(C1+C2)/(C1-C2)| < 40, \quad (11)$$

where f is the focal length of the entire system, f1 is the focal length of the first group G1', f2 is the focal length of the second group G2', f3 is the focal length of the third group G3', f4 is the focal length of the fourth group G4', C1 is the curvature of the object-side surface of the meniscus lens L1' in the first group G1', and C2 is the curvature of the image-side surface of the meniscus lens L1' in the first group G1'.

As described in Patent Literatures 2 and 3, because the objective lens is small, it is effective to employ a configuration in which the aperture is disposed on the object side, and in which a positive first group and a positive second group are included. However, when the angle of view is set to have a wide viewing angle equal to or greater than 100°, it is not possible to sufficiently suppress the off-axis aberration, which is necessary to ensure the performance to be compatible with a high-definition imaging device. Therefore, in the present invention, by employing the configuration including, in order from the object side, the aperture stop, the positive first group, the second group, the positive third group, and the fourth group, it is possible to satisfactorily correct off-axis aberrations (comatic aberration, astigmatic difference, and field curvature) and to suppress the occurrence thereof even with a wide angle of view. In particular, it is possible to keep the Petzval sum low due to the power distribution of the four-group configuration.

In addition, with the present invention, it is possible to gradually increase the distance between an off-axis beam and the center optical axis toward the image side from the aperture stop disposed closest to the object side, and thus, it is possible to correct the comatic aberration occurring in the first group at the second group, as well as the third and fourth groups, while keeping the influences on the on-axis performance, the focal length, and the overall length low. The configurations in Patent Literatures 1 and 6 are not suitable for achieving size reduction because the aperture stop is disposed at an intermediate position in the optical system. On the other hand, with the second aspect of the present invention, it is possible to achieve a wide-angle objective optical system having an angle of view equal to or greater than 100° with a small number of lenses.

In addition, in the first group, the surface closest to the object side is a concave or flat surface toward the object side, the surface closest to the image side is convex toward the image side, and thus, the principal point of the first group can be moved away from the aperture stop toward the image side. By doing so, the power arrangement of the first group can be made substantially concentric with respect to the aperture, which makes it possible to suppress the occurrence of an astigmatic difference and off-axis comatic aberration.

In addition, in order to ensure performance that is compatible with a wide-angle, high-definition imaging device, it is necessary to sufficiently suppress the magnification chromatic aberration. In the present invention, the magnification chromatic aberration is satisfactorily corrected by employing a cemented lens in the third group. On the other hand, in the case of Patent Literature 4, it is difficult to sufficiently correct the magnification chromatic aberration when a wide viewing angle is achieved because no cemented lens is included.

In addition, by setting the power of the fourth group within an appropriate range in accordance with Conditional Expression (7), it is possible to satisfactorily correct aberrations. When f/f4 is equal to or less than the lower limit of −0.5, because the power of the fourth group becomes relatively high, the off-axis image plane becomes inclined due to overcorrection of the Petzval sum and the comatic aberration is also increased, which decrease the image quality. On the other hand, when f/f4 is equal to or greater than the upper limit of −0.001, because the power of the fourth group becomes relatively low, it is not possible to sufficiently correct the field curvature, which decreases the image quality.

In addition, by setting the relative power ratio between the second group and the fourth group in accordance with Conditional Expression (8), field curvature and comatic aberration occurring in the second group can satisfactorily be corrected at the fourth group. When |f4/f2| is greater than the upper limit of 5, the occurrence of aberrations increases in the second group, which makes sufficient correction thereof impossible at the fourth group. On the other hand, when |f4/f2| is less than the lower limit of 0.1, because the relative power of the second group becomes too low, which shifts the correction of the field curvature more toward the fourth group, the power of the fourth group becomes relatively high, which causes comatic aberration, and thus, the optical system as a whole becomes large.

In the present invention, it is preferable that Conditional Expression (9) is satisfied.

The cemented lens in the third group corrects chromatic aberration, and, at the same time, is also responsible for the power distribution of the entire system when a wider viewing angle is achieved. In Conditional Expression (9), when f/f3 is equal to or less than the lower limit of 0.3, the power of the first group increases, which decreases the performance. On the other hand, when f/f3 is equal to or greater than the upper limit of 0.8, the power of the third group increases, which decreases the edge thickness at the lens edge of the positive lens that forms the cemented lens in the third group, which makes fabrication of the cemented lens difficult.

In the present invention, it is preferable that Conditional Expression (10) is satisfied.

In Conditional Expression (10), when f/f1 is equal to or less than the lower limit of 0.15, the power of the third group becomes relatively high, which causes the off-axis performance to deteriorate. On the other hand, when f/f1 is equal to or greater than the upper limit of 1.1, the power of the first group becomes relatively high, which increases the occurrence of comatic aberration, and thus, it is difficult to sufficiently correct the comatic aberration at the second and fourth groups.

In the present invention, it is preferable that the first group satisfy Conditional Expression (11).

In Conditional Expression (11), when |(C1+C2)/(C1−C2)| is equal to or greater than the upper limit of 40, the amount of protrusion of the convex surface of the meniscus lens increases, making it thicker. In addition, it becomes difficult to ensure a sufficient edge thickness at the lens edge. On the other hand, when |(C1+C2)/(C1−C2)| is less than the lower limit of 1, the shape of the meniscus lens or the plano-convex lens approaches the shape of a double-convex lens, and because this causes the curvature thereof to deviate from the concentric state with respect to the aperture stop, the astigmatic difference increases, which decreases the off-axis performance.

Although having a small size and a wide viewing angle, the thus-configured objective optical system 1' according to this embodiment satisfactorily corrects aberrations, and therefore, the objective optical system 1' is also suitably compatible with a high-definition, high-pixel-count solid-state imaging device.

Note that, in this embodiment, it is more preferable that the objective optical system 1' satisfy Conditional Expressions (7)', (8)', and (11)' below:

$$-0.5 < f/f4 < -0.05, \quad (7)'$$

$$0.7 \leq |f4/f2| \leq 3, \text{ and} \quad (8)'$$

$$-25 < (C1+C2)/(C1-C2) < -2. \quad (11)'$$

In addition, in this embodiment, although the first group G1' is formed of the single meniscus lens L1', alternatively, the first group G1' may be formed of a single plano-convex lens whose convex surface faces the image side.

Examples of Second Embodiment

Next, Examples 1 to 5 of the above-described second embodiment will be described with reference to FIGS. 11 to 20.

Example 1

Figure 11:
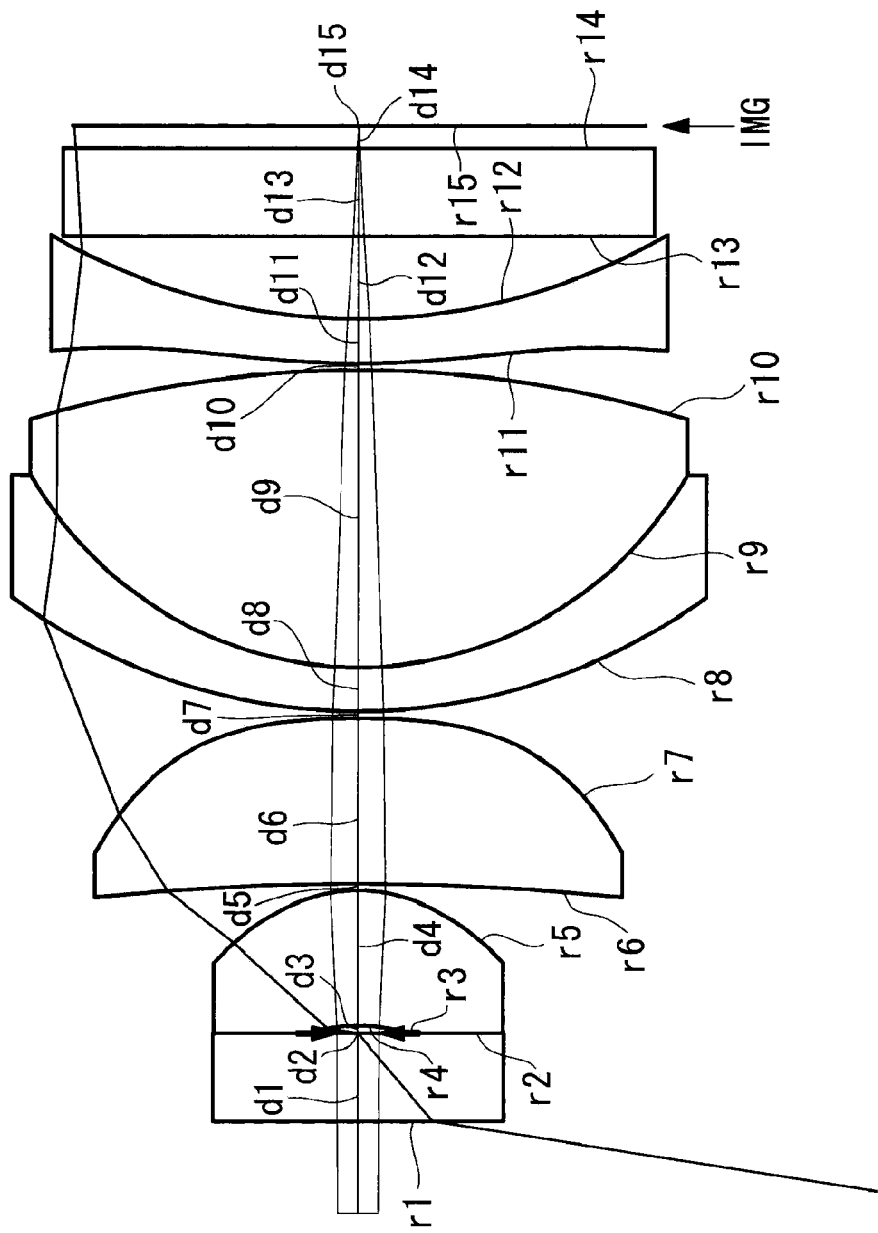
FIG. 11 is a cross-sectional view of a lens showing the overall configuration of the objective optical system according to Example 1 of the second embodiment of the present invention.
Figure 12:
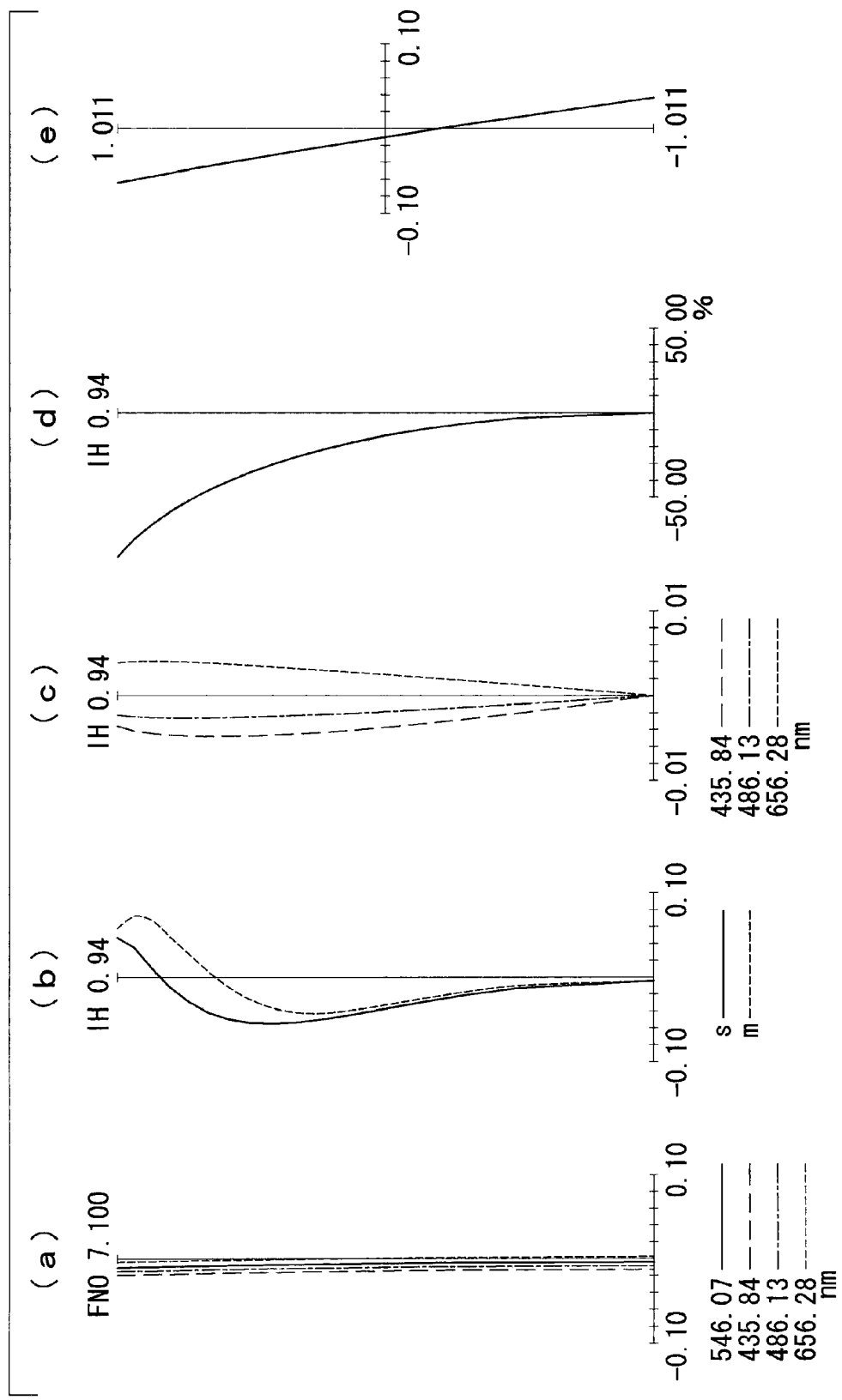
FIG. 12 is a diagram showing various types of aberration of the objective optical system in FIG. 11.

As shown in FIG. 11, in an objective optical system according to Example 1 of the second embodiment, the first group is formed of a single meniscus lens whose convex surface faces the image side; the second group is formed of a single meniscus lens whose convex surface faces the image side; the third group is formed of a cemented lens including a negative meniscus lens, whose convex surface faces the object side, and a double-convex lens; and the fourth group is formed of a single meniscus lens whose convex surface faces the object side. FIG. 12 shows aberration diagrams of the thus-configured objective optical system of this Example.

Although the objective optical system according to this Example is compact, having an overall length of about 3.4 times the image height, an angle of view of 162° can be achieved. One reason for this is that the power of the first group is successfully kept relatively low by effectively utilizing the aspheric surfaces employed in the first group, the second group, and the fourth group. The refractive indexes and the Abbe numbers of the first group, the second group, and the fourth group are those for optical members made of plastic materials so that the aspheric surfaces thereof can be fabricated at low cost.

In addition, the power arrangement of the cemented lens in the third group and the selection of glasses are satisfactory, and thus, it is possible to satisfactorily correct the magnification chromatic aberration. Specifically, the value of the left side of the Expression below, which defines the achromatizing condition for a general cemented lens, is 0.0002, thus being extremely low and sufficiently satisfying the condition:

$$1/(f31 \times vd31) + 1/(f32 \times vd32) = 0,$$

where f31 is the focal length of the negative meniscus lens in the third group, vd31 is the Abbe number of the material for the negative meniscus lens in the third group, f32 is the focal length of the double-convex lens in the third group, and vd32 is the Abbe number of the material for the double-convex lens in the third group.

| Lens Data | | | | | |
|---|---|---|---|---|---|
| Surface Number | r | d | ne | Vd | ER |
| OBJ | ∞ | 10.7407 | 1.00000 | | |
| 1 | ∞ | 0.2864 | 1.51825 | 64.14 | 0.444 |
| 2 | ∞ | 0.0000 | 1.00000 | | 0.070 |
| 3(S) | ∞ | 0.0251 | 1.00000 | | 0.070 |
| 4 | −0.5647 | 0.4382 | 1.53336 | 56.00 | 0.131 |
| 5* | −0.5087 | 0.0215 | 1.00000 | | 0.441 |
| 6 | −8.5360 | 0.5384 | 1.53336 | 56.00 | 0.706 |
| 7* | −2.6765 | 0.0215 | 1.00000 | | 0.835 |
| 8 | 1.9649 | 0.1432 | 1.93429 | 18.90 | 1.111 |
| 9 | 1.2552 | 0.9619 | 1.73234 | 54.68 | 1.050 |
| 10 | −3.7653 | 0.0215 | 1.00000 | | 1.043 |
| 11* | 3.0262 | 0.1432 | 1.53336 | 56.00 | 0.983 |
| 12 | 2.0404 | 0.2688 | 1.00000 | | 0.933 |
| 13 | ∞ | 0.2864 | 1.51825 | 64.14 | 0.935 |
| 14 | ∞ | 0.0716 | 1.00000 | | 0.941 |
| 15 | ∞ | 0.0000 | 1.00000 | | 0.944 |
| IMG | ∞ | 0.0000 | | | |

| Aspheric Surface Data |
|---|
| Surface 5 |
| r = −0.5087    K = −0.5730 |
| A4 = 3.4135E−01    A6 = −1.6667E−01 |

| Surface 7 |
|---|
| r = −2.6765    K = 0.3236 |
| A4 = −5.6866E−01    A6 = 2.9915E−01 |
| A8 = −2.9358E−01 |

| Surface 11 |
|---|
| r = 3.0262    K = −0.7326 |
| A4 = −1.2124E−01    A6 = −5.2156E−02 |
| A8 = 4.9143E−02 |

| Miscellaneous data | |
|---|---|
| Focal length | 1.0 |
| Image height | 0.942 |
| Fno. | 7.1 |
| Effective Fno. | 7.316 |
| Distance to object point | 10.7407 |
| Half-angle of view | 81.0 |
| Distortion | −85.3% |

Example 2

Figure 13:
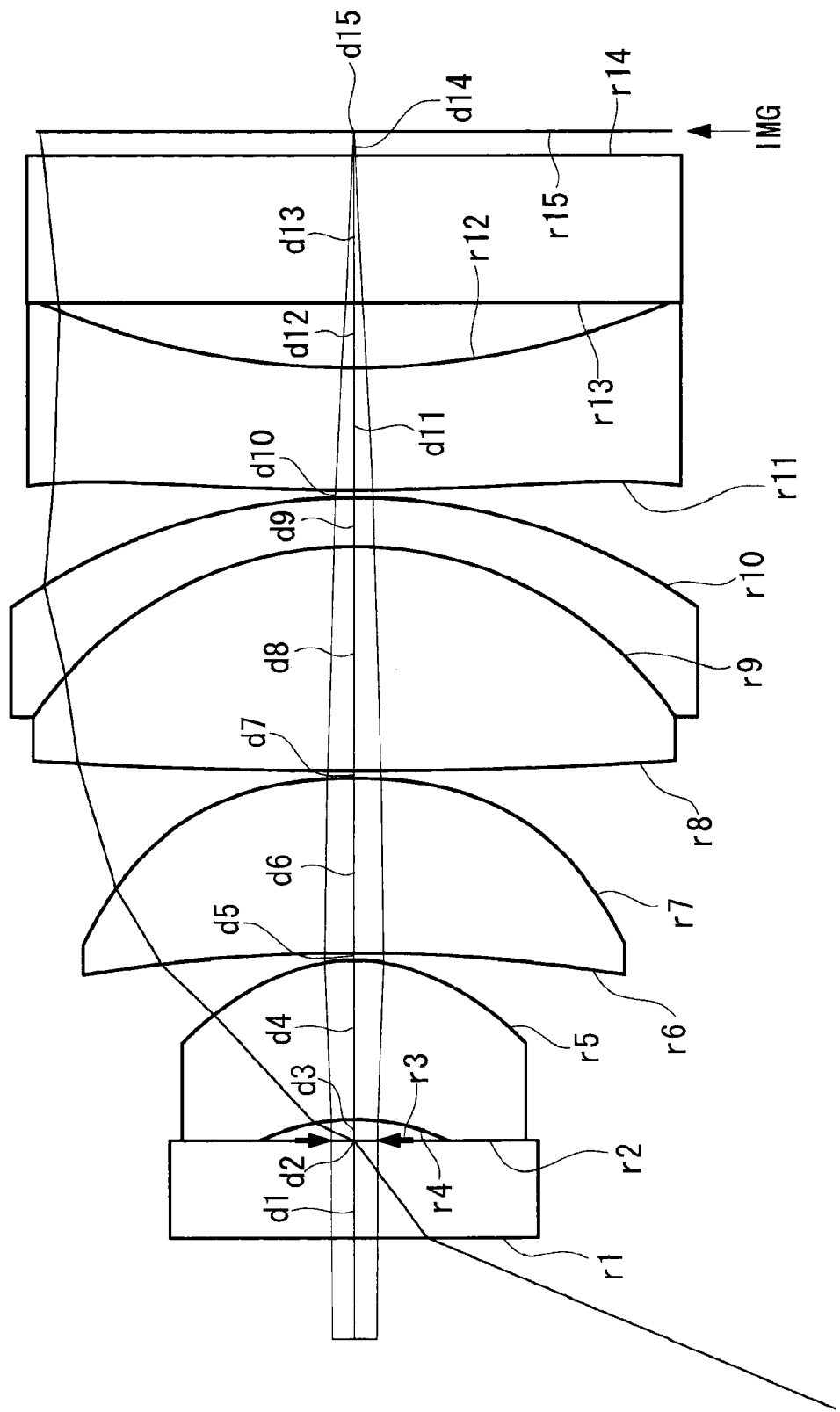
FIG. 13 is a cross-sectional view of a lens showing the overall configuration of the objective optical system according to Example 2 of the second embodiment of the present invention.
Figure 14:
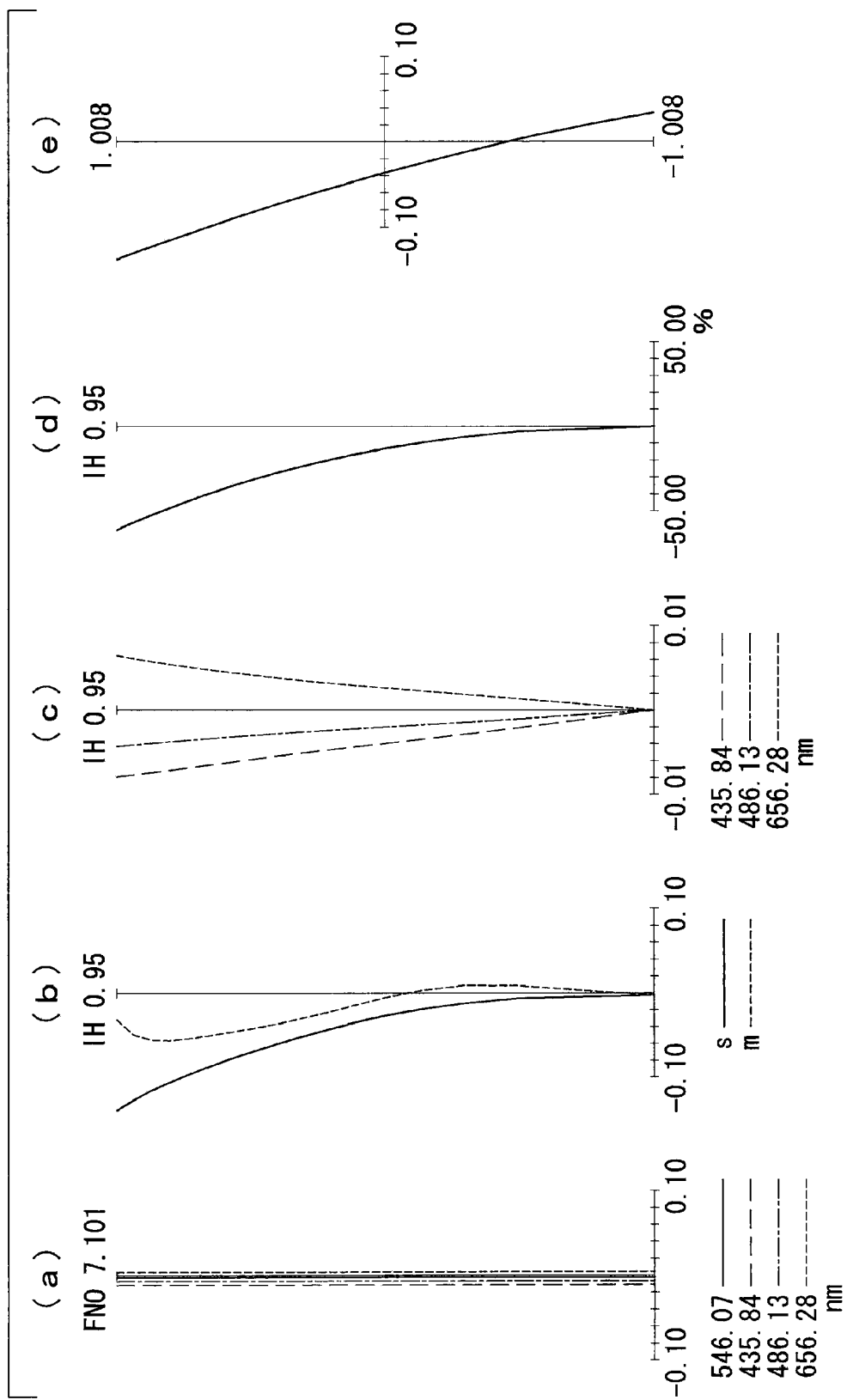
FIG. 14 is a diagram showing various types of aberration of the objective optical system in FIG. 13.

As shown in FIG. 13, in an objective optical system according to Example 2 of the second embodiment, the first group is formed of a single meniscus lens whose convex surface faces the image side; the second group is formed of a single meniscus lens whose convex surface faces the image side; the third group is formed of a cemented lens including a double-convex lens and a negative meniscus lens whose convex surface faces the image side; and the fourth group is formed of a single meniscus lens whose convex surface faces the object side. FIG. 14 shows aberration diagrams of the thus-configured objective optical system of this Example.

Although the objective optical system according to this Example is compact, having an overall length of about 3.4 times the image height, an angle of view of 134° can be achieved. In addition, by disposing the double-convex lens and the negative meniscus lens in this order from the object side in the cemented lens in the third group, the curvature of the double-convex lens on the object side can be made relatively gentle, and thus, the processability can be enhanced.

In addition, the power arrangement of the cemented lens in the third group and the selection of glasses are satisfactory, and thus, it is possible to satisfactorily correct the magnification chromatic aberration. Specifically, the value of the left side of the Expression below, which defines the achromatizing condition for a general cemented lens, is −0.0009, thus being extremely low and sufficiently satisfying the condition:

$$1/(f31 \times vd31) + 1/(f32 \times vd32) = 0,$$

where f31 is the focal length of the double-convex lens in the third group, vd31 is the Abbe number of the material for the double-convex lens in the third group, f32 is the focal length of the negative meniscus lens in the third group, and vd32 is the Abbe number of the material for the negative meniscus lens in the third group.

| Lens Data | | | | | |
|---|---|---|---|---|---|
| Surface Number | r | d | ne | Vd | ER |
| OBJ | ∞ | 10.8206 | 1.00000 | | |
| 1 | ∞ | 0.2885 | 1.51825 | 64.14 | 0.505 |

-continued

| | | | | | |
|---|---|---|---|---|---|
| 2 | ∞ | 0.0000 | 1.00000 | | 0.070 |
| 3(S) | ∞ | 0.0606 | 1.00000 | | 0.070 |
| 4 | −0.6889 | 0.4743 | 1.53336 | 56.00 | 0.167 |
| 5* | −0.5236 | 0.0216 | 1.00000 | | 0.467 |
| 6 | −5.0892 | 0.5172 | 1.53336 | 56.00 | 0.663 |
| 7* | −1.5171 | 0.0216 | 1.00000 | | 0.766 |
| 8 | 15.8237 | 0.6654 | 1.73234 | 54.68 | 0.890 |
| 9 | −1.1797 | 0.1443 | 1.93429 | 18.90 | 0.917 |
| 10 | −1.8042 | 0.0216 | 1.00000 | | 0.984 |
| 11* | 7.1895 | 0.3607 | 1.53336 | 56.00 | 0.934 |
| 12 | 2.4561 | 0.1918 | 1.00000 | | 0.900 |
| 13 | ∞ | 0.4328 | 1.51825 | 64.14 | 0.902 |
| 14 | ∞ | 0.0721 | 1.00000 | | 0.938 |
| 15 | ∞ | 0.0000 | 1.00000 | | 0.949 |
| IMG | ∞ | 0.0000 | | | |

Aspheric Surface Data

Surface 5 r = −0.5236     K = −0.5602
A4 = 8.2684E−01     A6 = −8.8005E−01

Surface 7 r = −1.5171     K = 0.3086
A4 = −6.0835E−01     A6 = 3.5648E−01
A8 = −4.1914E−01

Surface 11 r = 7.1895     K = −0.8426
A4 = −3.2140E−02     A6 = −2.8034E−02
A8 = 9.1159E−04

Miscellaneous data

| | |
|---|---|
| Focal length | 1.0 |
| Image height | 0.949 |
| Fno. | 7.101 |
| Effective Fno. | 7.277 |
| Distance to object point | 10.8206 |
| Half-angle of view | 67.3 |
| Distortion | −61.7% |

Example 3

Figure 15:
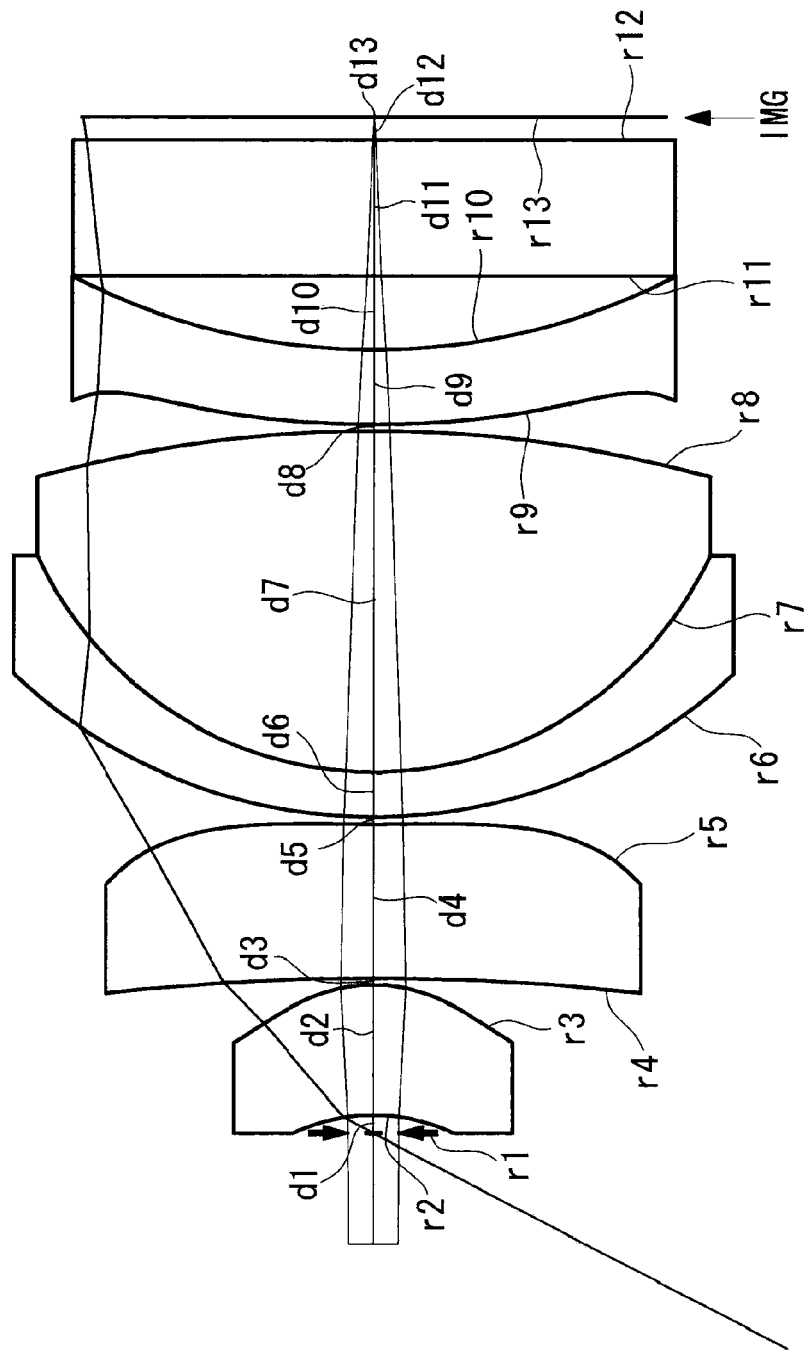
FIG. 15 is a cross-sectional view of a lens showing the overall configuration of the objective optical system according to Example 3 of the second embodiment of the present invention.
Figure 16:
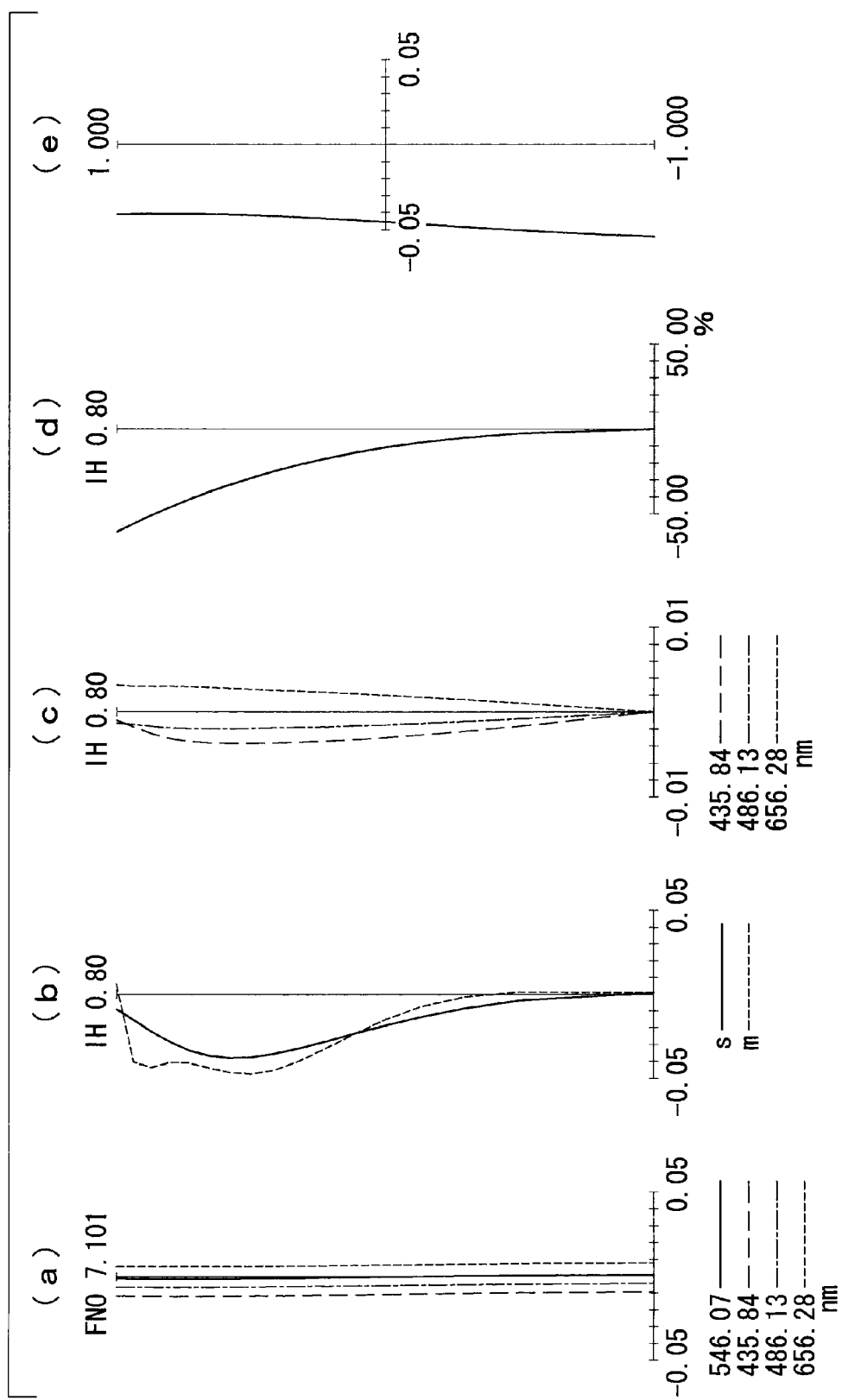
FIG. 16 is a diagram showing various types of aberration of the objective optical system in FIG. 15.

As shown in FIG. 15, in an objective optical system according to Example 3 of the second embodiment, the first group is formed of a single meniscus lens whose convex surface faces the image side; the second group is formed of a single meniscus lens whose convex surface faces the image side; the third group is formed of a cemented lens including a negative meniscus lens, whose convex surface faces the object side, and a double-convex lens; and the fourth group is formed of a single meniscus lens whose convex surface faces the object side. FIG. 16 shows aberration diagrams of the thus-configured objective optical system of this Example.

The objective optical system according to this Example is compact, having an overall length of about 3.4 times the image height. One reason for this is that the power distributions of the first group and the third group are kept moderate and satisfactory by effectively utilizing the aspheric surfaces employed in the first group, the second group, and the fourth group, and that the relationship between the power of the fourth group and that of the second group is satisfactory. In addition, the refractive indexes and the Abbe numbers of the first group, the second group, and the fourth group are those for optical members made of plastic materials so that the aspheric surfaces thereof can be fabricated at low cost.

In addition, the power arrangement of the cemented lens in the third group and the selection of glasses are satisfactory, and thus, it is possible to satisfactorily correct the magnification chromatic aberration. Specifically, the value of the left side of the Expression below, which defines the achromatizing condition for a general cemented lens, is 0.0031, thus being extremely low and sufficiently satisfying the condition:

$$1/(f31 \times vd31) + 1/(f32 \times vd32) = 0,$$

where f31 is the focal length of the negative meniscus lens in the third group, vd31 is the Abbe number of the material for the negative meniscus lens in the third group, f32 is the focal length of the double-convex lens in the third group, and vd32 is the Abbe number of the material for the double-convex lens in the third group.

Lens Data

| Surface Number | r | d | ne | Vd | ER |
|---|---|---|---|---|---|
| OBJ | ∞ | 9.1117 | 1.00000 | | |
| 1(S) | ∞ | 0.0486 | 1.00000 | | 0.070 |
| 2 | −0.5113 | 0.3505 | 1.53336 | 56.00 | 0.131 |
| 3* | −0.4118 | 0.0182 | 1.00000 | | 0.351 |
| 4 | −6.4926 | 0.4172 | 1.53336 | 56.00 | 0.512 |
| 5* | 9.6467 | 0.0182 | 1.00000 | | 0.703 |
| 6 | 1.4550 | 0.1215 | 1.93429 | 18.90 | 0.955 |
| 7 | 1.0228 | 0.9176 | 1.73234 | 54.68 | 0.891 |
| 8 | −3.4882 | 0.0182 | 1.00000 | | 0.869 |
| 9* | 2.9102 | 0.2005 | 1.53336 | 56.00 | 0.797 |
| 10 | 1.8246 | 0.1994 | 1.00000 | | 0.768 |
| 11 | ∞ | 0.3645 | 1.51825 | 64.14 | 0.771 |
| 12 | ∞ | 0.0607 | 1.00000 | | 0.795 |
| 13 | ∞ | 0.0000 | 1.00000 | | 0.801 |
| IMG | ∞ | 0.0000 | | | |

Aspheric Surface Data

Surface 3 r = −0.4118     K = −0.7823
A4 = 3.2237E−01     A6 = 7.0227E+00

Surface 5 r = 9.6467     K = −18.6012
A4 = −7.9835E−01     A6 = 8.6197E−01
A8 = −1.1310E+00

Surface 9 r = 2.9102     K = −0.5374
A4 = 8.0527E−02     A6 = 1.3508E−01
A8 = −6.2436E−01

Miscellaneous data

| | |
|---|---|
| Focal length | 1.0 |
| Image height | 0.799 |
| Fno. | 7.1 |
| Effective Fno. | 7.458 |
| Distance to object point | 9.1117 |
| Half-angle of view | 62.6 |
| Distortion | −60.6% |

Example 4

Figure 17:
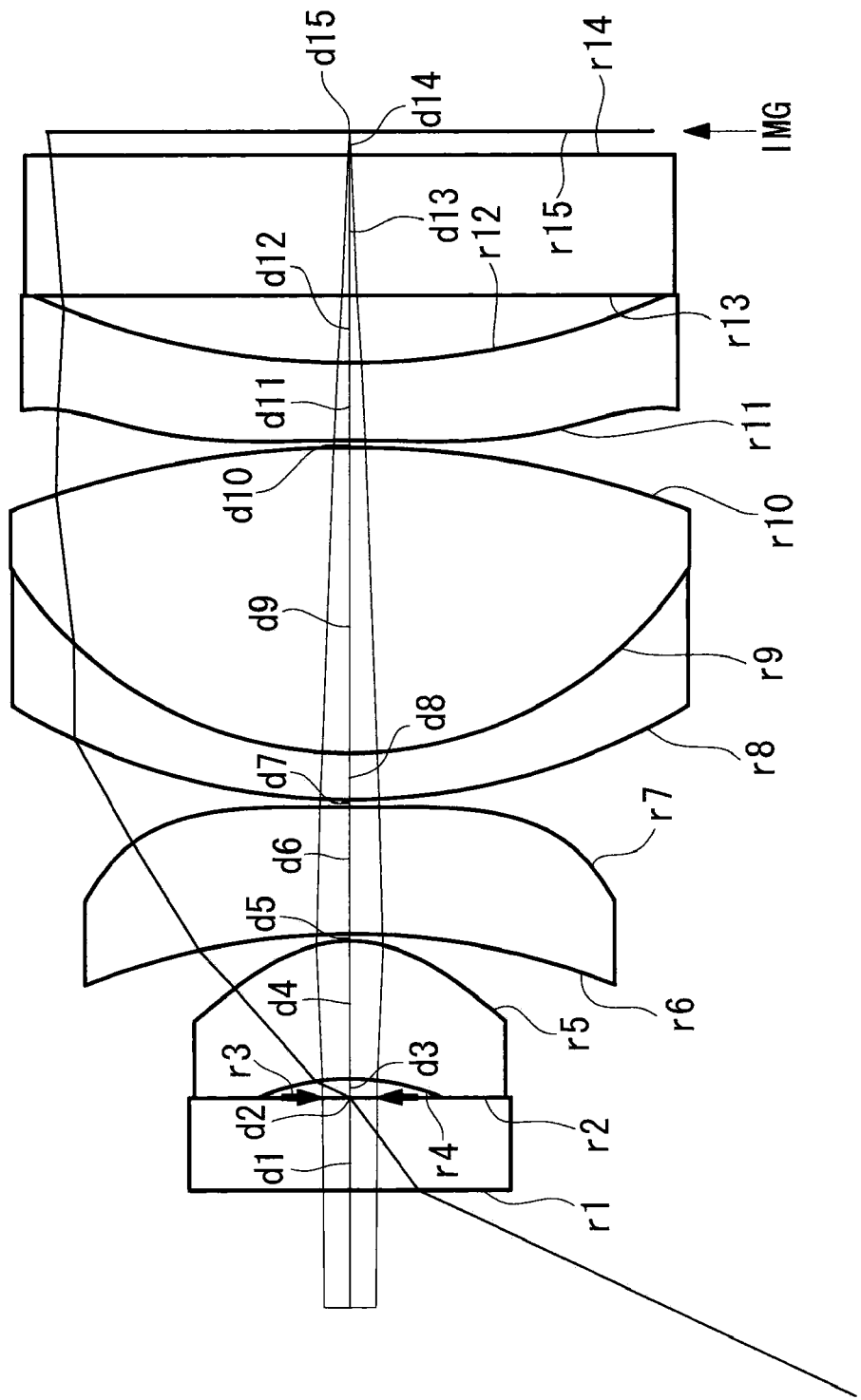
FIG. 17 is a cross-sectional view of a lens showing the overall configuration of the objective optical system according to Example 4 of the second embodiment of the present invention.
Figure 18:
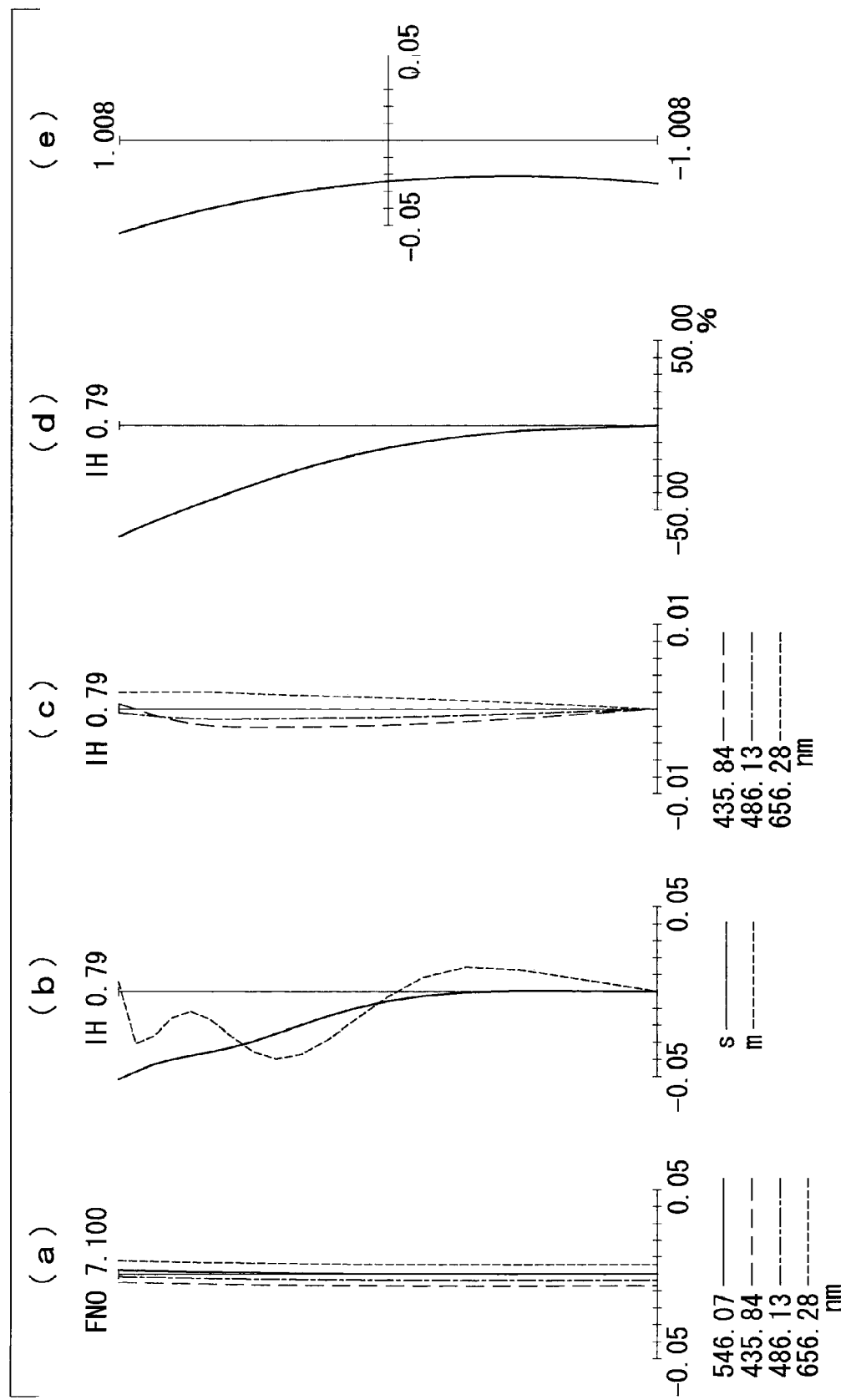
FIG. 18 is a diagram showing various types of aberration of the objective optical system in FIG. 17.

As shown in FIG. 17, in an objective optical system according to Example 4 of the second embodiment, the first group is formed of a single meniscus lens whose convex surface faces the image side; the second group is formed of a single meniscus lens whose convex surface faces the image side; the third group is formed of a cemented lens including a negative meniscus lens, whose convex surface faces the object side, and a double-convex lens; and the fourth group is formed of a single meniscus lens whose convex surface faces the object side. FIG. 18 shows aberration diagrams of the thus-configured objective optical system of this Example.

Although the objective optical system according to this Example is compact, having an overall length of about 3.5 times the image height, an angle of view of 130° can be achieved.

In addition, the power arrangement of the cemented lens in the third group and the selection of glasses are satisfactory, and thus, it is possible to satisfactorily correct the magnification chromatic aberration. Specifically, the value of the left side of the Expression below, which defines the achromatizing condition for a general cemented lens, is −0.0003, thus being extremely low and sufficiently satisfying the condition:

$$1/(f31 \times vd31) + 1/(f32 \times vd32) = 0,$$

where
f31 is the focal length of the negative meniscus lens in the third group,
vd31 is the Abbe number of the material for the negative meniscus lens in the third group,
f32 is the focal length of the double-convex lens in the third group, and
vd32 is the Abbe number of the material for the double-convex lens in the third group.

| Lens Data | | | | | |
|---|---|---|---|---|---|
| Surface Number | r | d | ne | Vd | ER |
| OBJ | ∞ | 8.9635 | 1.00000 | | |
| 1 | ∞ | 0.2390 | 1.51825 | 64.14 | 0.359 |
| 2 | ∞ | 0.0000 | 1.00000 | | 0.070 |
| 3(S) | ∞ | 0.0478 | 1.00000 | | 0.070 |
| 4 | −0.6162 | 0.3537 | 1.53336 | 56.00 | 0.139 |
| 5* | −0.3468 | 0.0179 | 1.00000 | | 0.345 |
| 6 | −1.8782 | 0.3257 | 1.53336 | 56.00 | 0.468 |
| 7* | 21.7650 | 0.0179 | 1.00000 | | 0.629 |
| 8 | 1.7277 | 0.1195 | 1.93429 | 18.90 | 0.819 |
| 9 | 1.0560 | 0.7833 | 1.73234 | 54.68 | 0.803 |
| 10 | −2.5053 | 0.0179 | 1.00000 | | 0.824 |
| 11* | −5.0382 | 0.1972 | 1.53336 | 56.00 | 0.793 |
| 12 | 2.0594 | 0.1733 | 1.00000 | | 0.768 |
| 13 | ∞ | 0.3585 | 1.51825 | 64.14 | 0.769 |
| 14 | ∞ | 0.0598 | 1.00000 | | 0.785 |
| 15 | ∞ | 0.0000 | 1.00000 | | 0.789 |
| IMG | ∞ | 0.0000 | | | |

| Aspheric Surface Data | |
|---|---|
| Surface 5 | |
| r = −0.3468 | K = −1.4851 |
| A4 = −5.9706E−01 | A6 = 3.8918E+00 |
| Surface 7 | |
| r = 21.7650 | K = −114.7633 |
| A4 = −1.0752E+00 | A6 = 1.0417E+00 |
| A8 = −2.3817E+00 | |
| Surface 11 | |
| r = −5.0382 | K = −4.6981 |
| A4 = 1.0055E+00 | A6 = −1.1993E+00 |
| A8 = 2.7826E−01 | |

| Miscellaneous data | |
|---|---|
| Focal length | 1.0 |
| Image height | 0.786 |
| Fno. | 7.1 |
| Effective Fno. | 7.608 |
| Distance to object point | 8.9635 |
| Half-angle of view | 65.0 |
| Distortion | −68.0% |

Example 5

Figure 19:
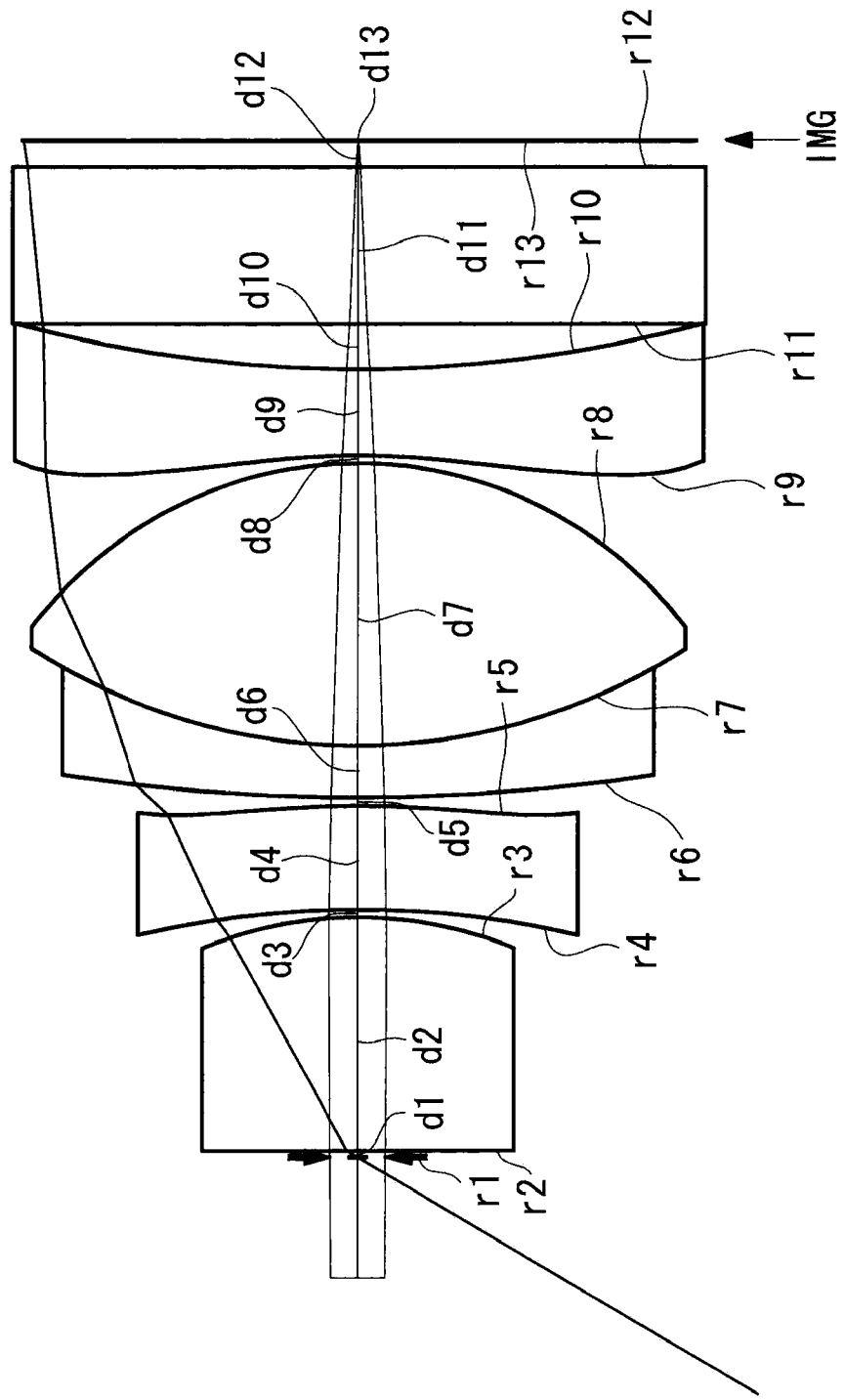
FIG. 19 is a cross-sectional view of a lens showing the overall configuration of the objective optical system according to Example 5 of the second embodiment of the present invention.
Figure 20:
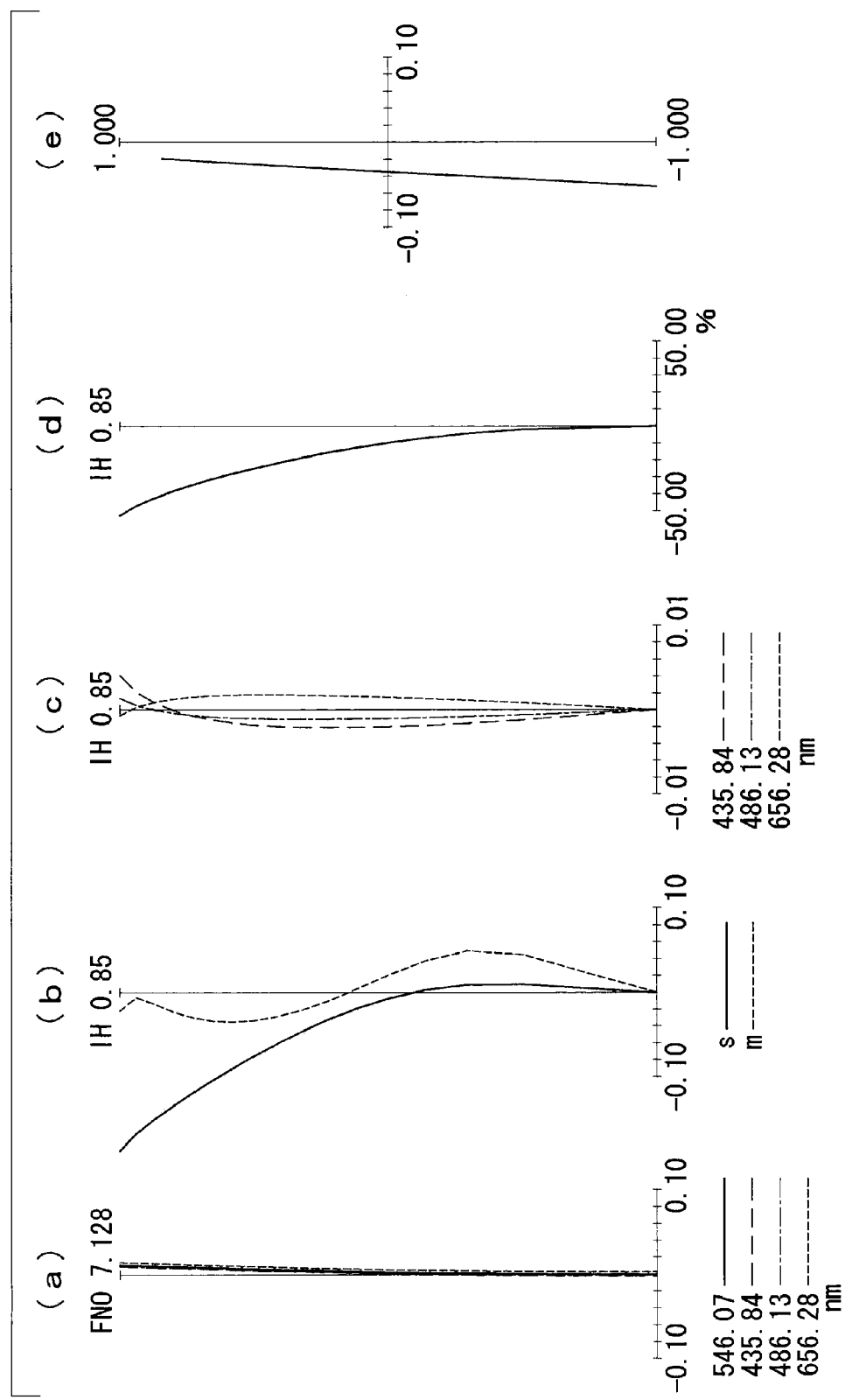
FIG. 20 is a diagram showing various types of aberration of the objective optical system in FIG. 19.

As shown in FIG. 19, in an objective optical system according to Example 5 of the second embodiment, the first group is formed of a single plano-convex lens whose convex surface faces the image side; the second group is formed of a single meniscus lens whose convex surface faces the image side; the third group is formed of a cemented lens including a negative meniscus lens, whose convex surface faces the object side, and a double-convex lens; and the fourth group is formed of a single lens. FIG. 20 shows aberration diagrams of the thus-configured objective optical system of this Example.

The objective optical system according to this Example is compact, having an overall length of about 3.0 times the image height.

In addition, the power arrangement of the cemented lens in the third group and the selection of glasses are satisfactory, and thus, it is possible to satisfactorily correct the magnification chromatic aberration. Specifically, the value of the left side of the Expression below, which defines the achromatizing condition for a general cemented lens, is −0.0045, thus being extremely low and sufficiently satisfying the condition:

$$1/(f31 \times vd31) + 1/(f32 \times vd32) = 0,$$

where
f31 is the focal length of the negative meniscus lens in the third group,
vd31 is the Abbe number of the material for the negative meniscus lens in the third group,
f32 is the focal length of the double-convex lens in the third group, and
vd32 is the Abbe number of the material for the double-convex lens in the third group.

In addition, because the first group is formed of a plano-convex lens, good processability can be achieved.

| Lens Data | | | | | |
|---|---|---|---|---|---|
| Surface Number | r | d | ne | Vd | ER |
| OBJ | ∞ | 9.7064 | 1.00000 | | |
| 1(S) | ∞ | 0.0162 | 1.00000 | | 0.070 |
| 2 | ∞ | 0.5824 | 1.77621 | 49.60 | 0.074 |
| 3 | −1.0505 | 0.0194 | 1.00000 | | 0.362 |
| 4 | −2.4612 | 0.2588 | 1.69417 | 31.07 | 0.400 |
| 5* | −1.9696 | 0.0194 | 1.00000 | | 0.525 |
| 6 | 5.0054 | 0.1294 | 1.93429 | 18.90 | 0.624 |
| 7 | 1.5479 | 0.7026 | 1.73234 | 54.68 | 0.716 |
| 8 | −1.0435 | 0.0194 | 1.00000 | | 0.796 |
| 9* | −1.8151 | 0.2135 | 1.53336 | 56.00 | 0.840 |
| 10 | 3.4045 | 0.1132 | 1.00000 | | 0.826 |
| 11 | ∞ | 0.3883 | 1.51825 | 64.14 | 0.827 |
| 12 | ∞ | 0.0647 | 1.00000 | | 0.846 |
| 13 | ∞ | 0.0000 | 1.00000 | | 0.857 |
| IMG | ∞ | 0.0000 | | | |

| Aspheric Surface Data | |
|---|---|
| Surface 5 | |
| r = −1.9696 | K = −101.6619 |
| A4 = −3.5827E−03 | A6 = 8.1097E−01 |
| A8 = −2.2443E−01 | |
| Surface 9 | |
| r = −1.8151 | K = −4.6873 |
| A4 = 5.2855E−01 | A6 = −7.2987E−01 |
| A8 = 5.3510E−01 | |

-continued

Miscellaneous data

| | |
|---|---|
| Focal length | 1.0 |
| Image height | 0.852 |
| Fno. | 7.1277 |
| Effective Fno. | 7.481 |
| Distance to object point | 9.7064 |
| Half-angle of view | 59.7 |
| Distortion | −55.4% |

Table 2 shows values of Conditional Expressions (7) to (11) for the objective optical systems according to Examples 1 to 5 of the second embodiment.

TABLE 2

| Conditional Expression | Example 1 | Example 2 | Example 3 | Example 4 | Example 5 |
|---|---|---|---|---|---|
| (7) | −0.081 | −0.139 | −0.102 | −0.368 | −0.457 |
| (8) | 1.746 | 1.862 | 1.359 | 0.841 | 0.187 |
| (f4/f2) | (−1.746) | (−1.862) | (−1.359) | −0.841 | (−0.187) |
| (9) | 0.473 | 0.391 | 0.604 | 0.591 | 0.734 |
| (10) | 0.387 | 0.488 | 0.561 | 0.979 | 0.739 |
| (11) | 19.163 | 7.335 | 9.276 | 3.575 | 1.000 |
| (11)' | −19.163 | −7.335 | −9.276 | −3.575 | −1.000 |

The following inventions can be derived from the above-described Examples 1 to 5 of the second embodiment.

{Additional Item 1}

An objective optical system formed of, in order from the object side, an aperture stop, a positive first group, a second group, a positive third group, and a fourth group, wherein the first group is formed of a single meniscus lens whose convex surface faces the image side, the second group is formed of a single lens, the third group is formed of a cemented lens including a positive lens and a negative lens, the fourth group is formed of a single lens, and Conditional Expressions (7)' and (8)' below are satisfied:

$$-0.5 < f/f4 < -0.05, \text{ and} \quad (7)'$$

$$0.7 \leq |f4/f2| \leq 3, \quad (8)'$$

where f is the focal length of the entire system, f4 is the focal length of the fourth group, and f2 is the focal length of the second group.

With the objective optical system of Additional Item 1, by employing a meniscus lens whose convex surface faces the image side as the first group, because the principal point can be disposed closer to the image side and because the curvature can be made concentric with respect to the aperture stop, it is possible to suppress the occurrence of an astigmatic difference. In addition, by determining the power of the fourth group in accordance with Conditional Expression (7)', it is possible to satisfactorily correct the field curvature. In addition, by determining the ratio between the power of the second group and the power of the fourth group in accordance with Conditional Expression (8)', it is possible to satisfactorily correct the field curvature and the comatic aberration, and it is also possible to achieve an overall size reduction of the lenses. {Additional Item 2}

An objective optical system according to Additional Item 1, satisfying Conditional Expression (9) below:

$$0.3 < f/f3 < 0.8, \quad (9)$$

where f3 is the focal length of the third group.

{Additional Item 3}

An objective optical system according to Additional Item 2, satisfying Conditional Expression (10) below:

$$0.15 < f/f1 < 1.1, \quad (10)$$

where f1 is the focal length of the first group.

{Additional Item 4}

An objective optical system according to Additional Item 3, wherein the first group satisfies Conditional Expression (11)' below:

$$-25 < (C1+C2)/(C1-C2) < -2, \quad (11)'$$

where C1 is the curvature of the object-side surface of the first group, and C2 is the curvature of the image-side surface of the first group.

With the objective optical system of Additional Item 4, the shape of the meniscus lens determined by Conditional Expression (11)' is effective for handling a wider viewing angle and high-definition image quality. In Conditional Expression (11)', when the value is equal to or less than the lower limit of −25, the amount of protrusion of the convex surface of the meniscus lens increases, thus making the lens thicker, and it is also difficult to ensure a sufficient edge thickness at the lens edge. On the other hand, when the value is equal to or greater than the upper limit of −2, the shape of the meniscus lens approaches that of a plano-convex lens, and, because this causes the curvature thereof to deviate from the concentric state with respect to the aperture stop, the astigmatic difference increases, thus decreasing the off-axis performance.

Third Embodiment

Next, an objective optical system 1″ according to a third embodiment will be described with reference to FIG. 21.

Figure 21:
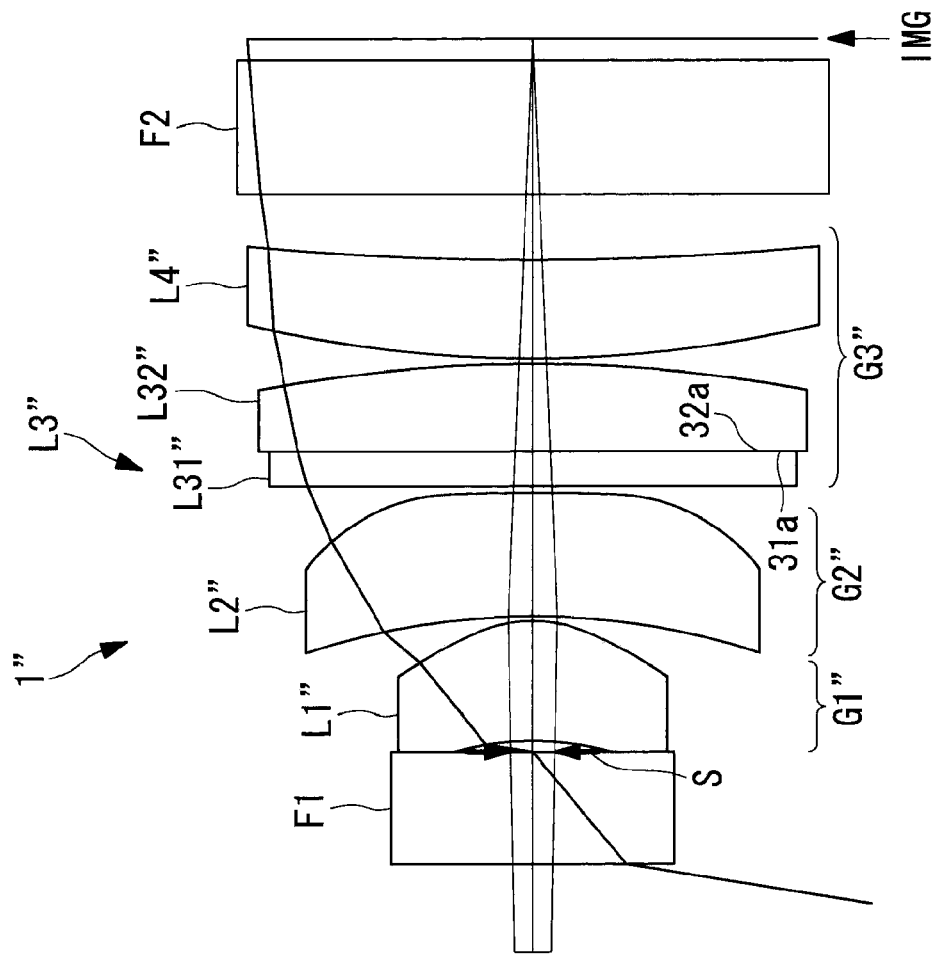
FIG. 21 is a diagram showing the overall configuration of an objective optical system according to a third embodiment.

As shown in FIG. 21, the objective optical system 1″ according to this embodiment is provided with, in order from the object side, an aperture stop S, a positive first group G1″, a second group G2″, and a positive third group G3″.

The first group G1″ is formed of a single meniscus lens L1″ whose convex surface faces the image side. Note that, the first group G1″ may be formed of a single plano-convex lens whose convex surface faces the image side, instead of the meniscus lens L1″.

The second group G2″ is formed of a single meniscus lens L2″.

The third group G3″ is formed of, in order from the object side, a lens L3″ including diffractive optical elements and a meniscus lens (another lens) L4″. The diffractive optical elements are lenses L31″ and L32″ having diffractive optical surfaces on which diffraction gratings are formed. The lens 3″ is formed by bringing diffractive optical surfaces 31a and 32a of the two lenses L31″ and L32″ into close contact with each other.

In addition, the objective optical system 1″ is provided with flat-parallel plates F1 and F2 at a portion closest to the object side and a portion closest to the image side, respectively.

The objective optical system 1″ satisfies the following Expressions (12) to (14):

$$-0.4 \leq f/f2 \leq -0.05, \quad (12)$$

$$0.1 \leq f/f3 \leq 0.4, \text{ and,} \quad (13)$$

$$0.001 \leq |f/f34| \leq 0.2, \quad (14)$$

where f2 is the focal length of the second group G2″, f3 is the focal length of the third group G3″, f is the focal length of the entire system, and f34 is the focal length of the another lens in the third group.

In the objective optical system 1", by employing the configuration including, in order from the object side, the aperture stop, the positive first group, the second group, and the positive third group, it is possible to satisfactorily correct off-axis aberrations (comatic aberration, astigmatic difference, and field curvature) and to suppress the occurrence thereof even with a wide angle of view. In particular, it is possible to keep the Petzval sum low due to the power distribution of the three-group configuration.

In addition, by forming the first group with a single meniscus lens or plano-convex lens, in which the convex surface faces the image side, it is possible to move the principal point of the first group away from the aperture stop toward image side; doing so makes the power arrangement of the first group substantially concentric with respect to the aperture; and thus, it is possible to suppress the occurrence of an astigmatic difference and off-axis comatic aberration.

In addition, with the configuration of the objective optical system 1", it is possible to gradually increase the distance between the off-axis beam and the center optical axis from the aperture stop, which is disposed closest to the object side, toward the image side. By doing so, it is possible to correct the comatic aberration occurring in the first group at the second group and the third group, while keeping the influence on the on-axis performance, the focal length, and the overall length low.

In order to ensure performance that is compatible with a wide-angle, high-definition imaging device, it is necessary to sufficiently suppress the magnification chromatic aberration. In the objective optical system 1", the magnification chromatic aberration is suppressed by including the diffractive optical element in the third group. In addition, because the thickness in the axial direction can be reduced in a diffractive optical element as compared with a conventional cemented lens, the diffractive optical element also contributes to reducing the overall length.

Here, the corrective effect of the diffractive optical element on chromatic aberration will briefly be described.

With a conventional refractive lens, when the lens is considered to be a thin lens whose intermediate thickness is assumed to be 0, the following Expression (100) holds, assuming that the radii of curvature at respective surfaces are R1 and R2, the refractive index of the medium is n, and the focal length is f.

$$1/f = (n-1)(1/R_1 - 1/R_2) \quad (100)$$

Figure 30:
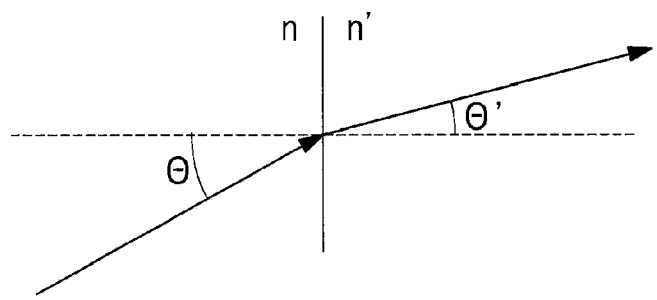
FIG. 30 is a diagram for explaining the principle of refraction of light.

As shown in FIG. 30, in the case of the refractive lens, a beam is refracted in accordance with Snell's law, given by Expression (200):

$$n \sin \theta = n' \sin \theta',$$

where n is the refractive index of the entrance-side medium, n' is the refractive index of the exit-side medium, $\theta$ is the angle of an entering beam, and $\theta'$ is the angle of an exiting beam.

Figure 31:
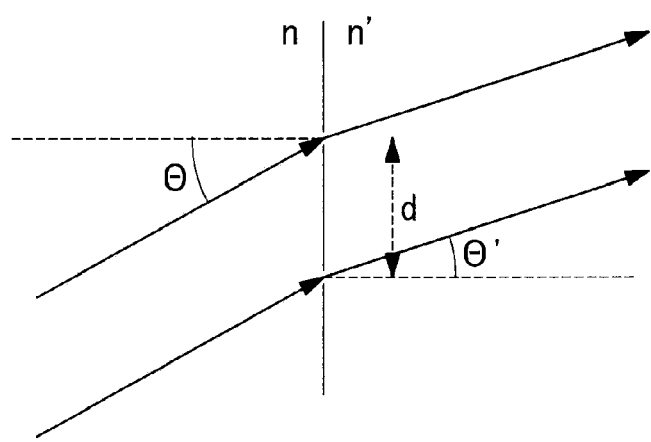
FIG. 31 is a diagram for explaining the principle of refraction of light in a diffraction grating.

Next, a general diffractive optical element will be described. A beam entering a diffraction grating having a grid spacing d as shown in FIG. 31 is diffracted in accordance with the following Expression (300):

$$n \sin \theta - n' \sin \theta' = m\lambda/d \quad (300)$$

$$(m = 0, \pm 1, \pm 2 \ldots),$$

where m is the diffraction order, and $\lambda$ is the wavelength of the light.

Here, by differentiating both sides of Expression (100) with respect to the wavelength $\lambda$, the following Expression (400) is obtained:

$$df/d\lambda = -f(dn/d\lambda)/(n-1)$$

$$\Delta f = -f\Delta n/(n-1). \quad (400)$$

In addition, by assuming that $f_{doe}$ is the focal length of the diffractive optical element, h is the ray height of the entering beam, $d_h$ is the grid spacing for the ray height h, and by substituting the result of setting $\theta = 0$ in Expression (300), the following Expression (500) is derived:

$$f_{doe} = h/(n'^* \sin \theta') = d_h h/m\lambda. \quad (500)$$

Because $d_h h$ is constant, Expression (500) can be expressed as $f = C/\lambda$ (C=constant). By differentiating both sides of this Expression with respect to $\lambda$, the following Expression (600) holds:

$$df/d\lambda = -C/\lambda^2 = -f/\lambda$$

$$\Delta f = -f(\Delta \lambda/\lambda). \quad (600)$$

Here, because the Abbe number $\nu$ is such that $\nu = (n-1)/\Delta n$, $\nu = \lambda/\Delta \lambda$ based on Expression (400) and Expression (600). Therefore, the Abbe number $\nu d$ of the diffractive optical element in the visible light region is as follows:

$$\nu_d = \lambda_d/(\lambda_F - \lambda_c) = -3.453.$$

As described above, a diffractive optical element possesses a high negative dispersion property. Because the Abbe number of ordinary optical glasses is from 20 to 95, a diffractive optical element possesses an extremely high inverse dispersion property. Therefore, combining an ordinary lens and a diffractive optical element is highly effective in removing on-axis chromatic aberration and magnification chromatic aberration.

In the objective optical system 1", it is preferable that Conditional Expressions (12) and (13).

By setting the power of the second group negative in accordance with Conditional Expression (12), the overall Petzval sum is reduced, and thus, it is possible to correct the field curvature. However, when f/f2 exceeds the upper limit of −0.05, the correction of the Petzval sum is decreased, which causes the off-axis image plane to be inclined, thus decreasing the image quality. On the other hand, when f/f2 falls below the lower limit of −0.4, although the Petzval sum can satisfactorily be corrected, it becomes impossible to maintain the balance of comatic aberration, thus decreasing the image quality.

By setting the power of the third group within an appropriate range in accordance with the Conditional Expression (13), it is possible to satisfactorily correct aberrations. When f/f3 exceeds the upper limit of 0.4 and the power of the third group is increased, the Petzval sum increases, which causes the off-axis image plane to be inclined, thus decreasing the image quality. On the other hand, when f/f3 falls below the lower limit of 0.1, which decreases the power of the third group, comatic aberration occurring in the first group increases because the power of the first group increases, thus decreasing the image quality.

In the objective optical system 1", it is preferable that the third group be formed of, in order from the object side, a lens including the diffractive optical element and another lens.

As described above, the functions of the third group are to correct the magnification chromatic aberration by using the diffractive optical element, and to adjust the field curvature and the direction in which a beam enters the image plane by utilizing the separation of on-axis and off-axis. By dividing the third group into a lens including the diffractive optical element and another lens, it becomes easier to allocate these functions to the respective lenses, which makes it possible to achieve an even wider viewing angle.

In the above-described configuration, it is preferable that Conditional Expression (14) be satisfied.

By setting the power of the other lens in the third group within an appropriate range in accordance with Conditional Expression (14), it is possible to satisfactorily correct aberrations. When |f/f34| exceeds the upper limit of 0.2, the Petzval sum increases, which causes the off-axis image plane to be inclined, thus decreasing the image quality. On the other hand, when |f/f34| falls below the lower limit of 0.001, which decreases the power, it is difficult to achieve a wider viewing angle because the ability to adjust the field curvature and the direction in which a beam enters the image plane is considerably decreased.

With the thus-configured objective optical system $1''$ according to this embodiment, because aberrations are satisfactorily corrected, the objective optical system $1''$ can suitably be employed in a high-definition, high-pixel-count solid-state imaging device and can also realize a size reduction, as well as a wider viewing angle.

Here, a closely laminated diffractive optical element will be described.

Because the diffraction efficiency of a single-layer diffraction grating depends on wavelength, by laminating diffraction gratings, the wavelength dependence can be eliminated, and high diffraction efficiency can also be achieved. A closely laminated diffractive optical element is an optical element in which diffractive optical surfaces of two diffraction gratings are laminated by bringing them into close contact with each other.

Figure 33:
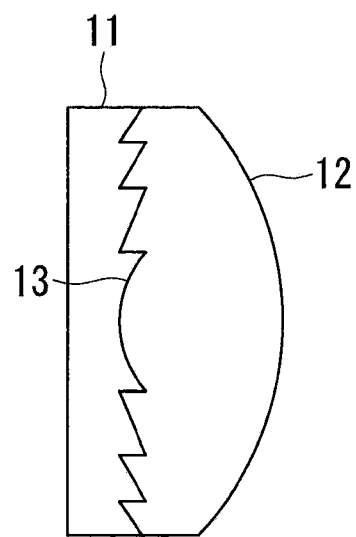
FIG. 33 is a diagram showing an example configuration of a closely laminated diffractive optical element.
Figure 34:
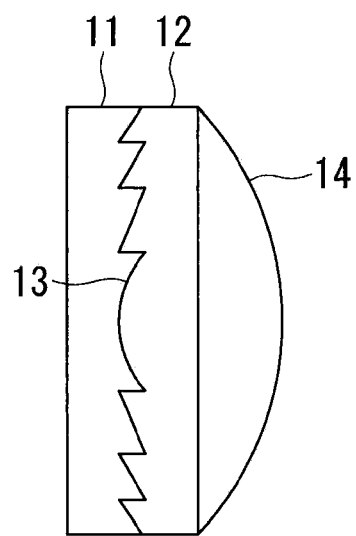
FIG. 34 is a diagram showing another example configuration of the closely laminated diffractive optical element.

FIGS. 33 and 34 are schematic diagrams of closely laminated diffractive optical elements.

In FIG. 33, a closely laminated diffractive optical element is formed of two diffractive optical elements 11 and 12. Materials forming the diffractive optical elements 11 and 12 are employed so as to form a combination of a refractive index and dispersion having low wavelength dependence and satisfactory diffraction efficiency. Reference sign 13 indicates diffractive optical surfaces. The diffractive optical element 12 possesses a refractive effect by virtue of a convex surface at a surface that is not a diffractive optical surface.

FIG. 34 shows an example in which a closely laminated diffractive optical element is formed on the flat-surface side of a general polished-glass plano-convex lens 14 that serves as a substrate. As with FIG. 33, the diffractive optical elements 11 and 12 are formed of materials employed so as to form a combination of refractive index and dispersion with low wavelength dependence and satisfactory diffraction efficiency.

Note that, regarding closely laminated diffractive optical elements, as well as combinations of materials that achieve high diffraction efficiency in closely laminated diffractive optical elements, detailed descriptions are included in "Introduction to Diffractive Optical Elements, revised and expanded edition (Optronics Co., Ltd., published on Feb. 8, 2006)" and so forth.

Examples of Third Embodiment

Next, Examples of the above-described third embodiment will be described.

Note that, in Miscellaneous data, f is the focal length of the entire system, Fno. is the F number, 2ω is the angle of view, and IH is the image height. These values are normalized by assuming that the focal length is 1. In addition, the d line is a spectral line at the wavelength of 587.56 nm, the C line is a spectral line at the wavelength of 656.27 nm, the e line is a spectral line at the wavelength of 546.07 nm, the F line is a spectral line at the wavelength of 486.13 nm, and the g line is a spectral line at the wavelength of 435.84 nm.

In addition, an aspheric surface is defined by the following Expression:

$$Z = CH^2 / \{(1-(1+K)(CH)^2)\}^{1/2} + A_4 H^4 + A_6 H^6 + A_8 H^8 + A_{10} H^{10},$$

where Z is the position of the aspheric surface in the optical-axis direction, H is the distance from the optical axis, C is the reciprocal of the radius of curvature, K is the cone constant, and $A_i$ (i=4, 6, 8, or 10) is an aspheric surface coefficient of $i^{th}$ order. However, when the value of the aspheric surface coefficient $A_i$ is zero, the description thereof is omitted in the aspheric surface data of the respective Examples.

Next, before describing the respective Examples, the high-refractive-index method (also known as the ultra-high index method (ultra-high index methods)), which is a method of designing an optical system including a diffractive optical element, will be described. The ultra-high index method is a method of designing a diffractive optical element by substituting a virtual lens (ultra-high index lens) having an extremely high refractive index.

Figure 32:
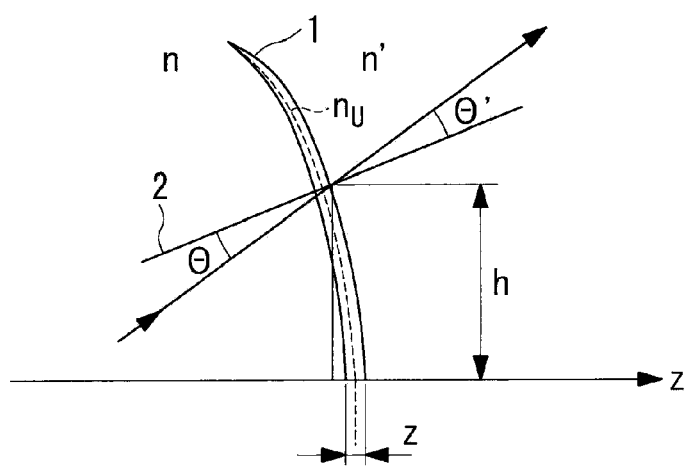
FIG. 32 is a diagram for explaining the relationship between Snell's law and the ultra-high index method.

With this ultra-high index lens, the following Expression holds:

$$(n_U - 1) dz/dh = n \sin \theta - n' \sin \theta', \quad (700)$$

where $n_U$ is the refractive index of a ultra-high index lens, z is a coordinate of the ultra-high index lens in the optical-axis direction, h is the distance from the optical axis, n and n' are refractive indexes of the entrance-side medium and the exit-side medium, respectively, and θ and θ' are the entering angle and the exiting angle of a beam, respectively. FIG. 32 illustrates the relationship among the individual parameters in Expression (700).

Based on Expressions (300) and (700), the following Expression (800) holds:

$$(n_U - 1) dz/dh = m\lambda/d. \quad (800)$$

Therefore, the equivalence relationship of Expression (800) holds between the surface shape of the ultra-high index lens and the pitch of the diffractive optical element. The pitch of the diffractive optical element can be determined from data designed by using the ultra-high index method based on this Expression (800).

On the other hand, a general axisymmetric aspheric-surface shape is given by the following Expression (900):

$$z = c h^2 / [1 + \{1-(1+k)c^2 h^2\}^{1/2}] + Ah^4 + Bh^6 + Ch^8 + Dh^{10} + \ldots, \quad (900)$$

where z is the optical axis (where the direction of an image is positive), c is the curvature of the reference surface, h is the coordinate axis in the meridional direction among coordinate axes perpendicular to the z axis with the origin set at the intersect between a plane and the z axis, k is the cone constant, and A, B, C, and D are fourth-order, sixth-order, eighth-order, and tenth-order aspheric surface coefficients, respectively.

Here, based on Expressions (800) and (900), the pitch d of a diffractive optical element equivalent to the above-described aspheric surface for a given ray height can be given by the following Expression:

$$d = m\lambda / [(n-1)\{ch/(1-c^2(1+k)h^2)^{1/2} + 4Ah^3 + 6Bh^5 + 8Ch^7 + 10Dh^9 + \ldots\}]. \quad (1000)$$

Therefore, it is possible to determine the surface shape of an equivalent diffractive lens based on the lens shape expressed in the form of an ultra-high index lens, and thus, it is possible to actually fabricate the lens.

Note that, regarding the ultra-high index method, detailed descriptions are included in the above-mentioned "Introduction to Diffractive Optical Elements, revised and expanded edition", and so forth.

Example 1

Figure 22:
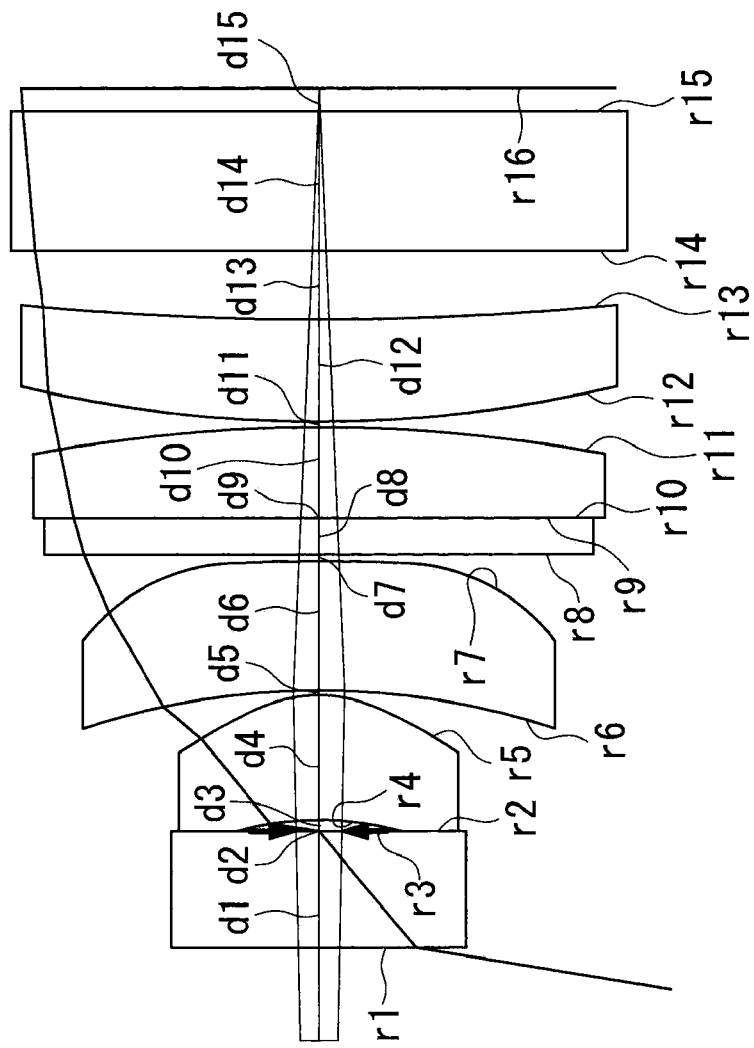
FIG. 22 is a cross-sectional view of a lens showing the overall configuration of the objective optical system according to Example 1 of the third embodiment.

As shown in FIG. 22 and the lens data below, an objective optical system according to Example 1 of the third embodiment is formed of, in order from the object side, a cover glass, an aperture stop, a first group formed of a positive meniscus lens whose convex surface faces the image side, a second group formed of a single lens, and a third group formed of a lens including diffractive optical elements and a lens in which the object-side surface thereof is an aspheric surface. The meniscus lens in the first group has an aspheric surface at the image-side surface where the curvature outward from the optical axis becomes gentle. The lens in the second group has an aspheric surface at the image-side surface.

The lens including the diffractive optical elements is a closely laminated diffractive optical element in which a material whose refractive index at the d line is 1.6 and whose Abbe number is 20 and a material whose refractive index at the d line is 1.75 and whose Abbe number is 33 are attached to each other. In addition, the surface shapes of the diffractive optical surfaces (9th surface and 10th surface) are given by the above-described ultra-high index method. Refractive indexes based on the ultra-high index method for the respective wavelengths at the 9th surface are as follows:
d line: 1001,
C line: 1117.941,
e line: 930.3859,
F line: 828.3708, and
g line: 742.7625.

An actual diffractive optical element can be fabricated by determining the surface shape of a closely laminated diffractive optical element in which the phase calculated by the ultra-high index method can be achieved with the aspheric-surface shape of the 10th surface.

Figure 23:
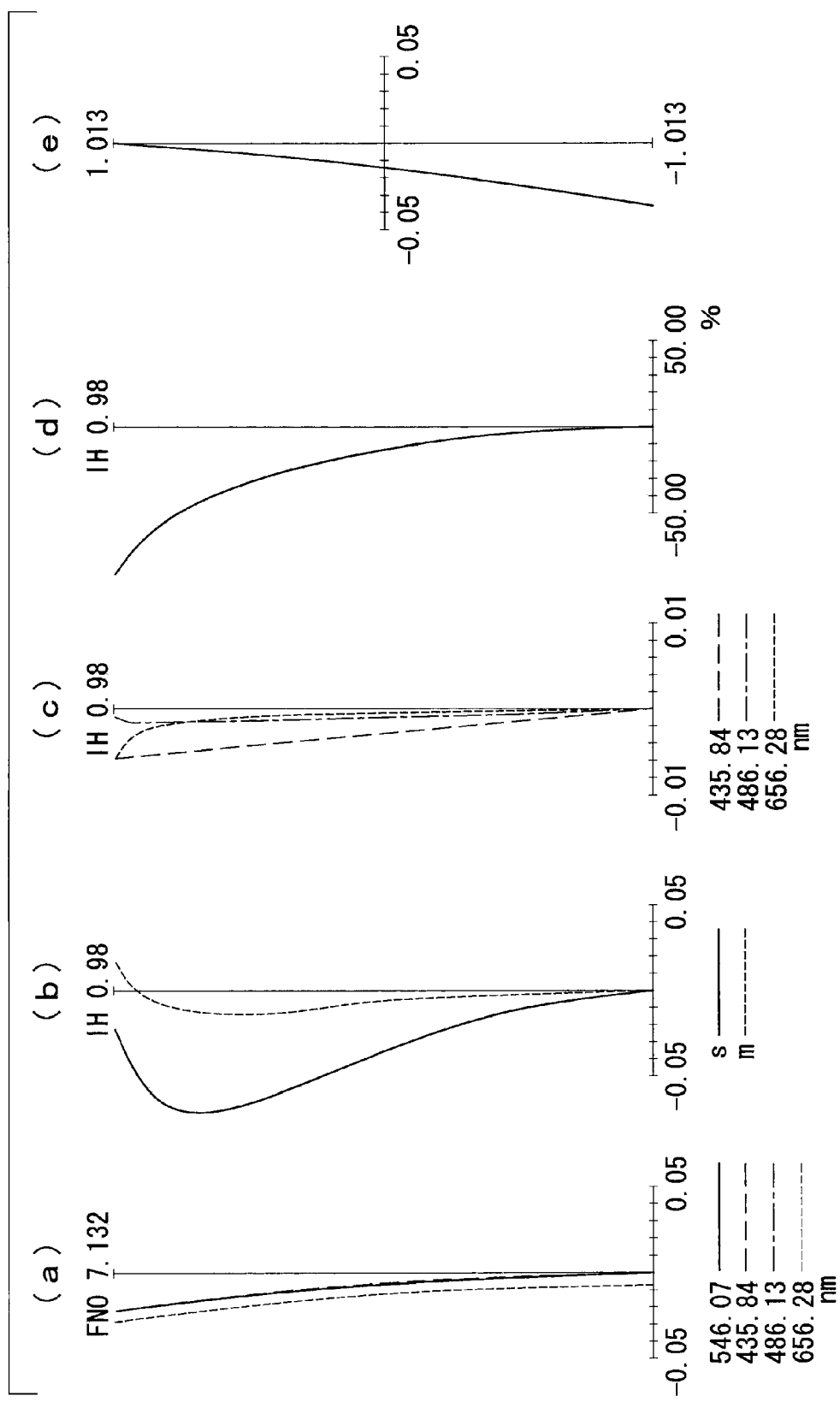
FIG. 23 is a diagram showing various types of aberration of the objective optical system in FIG. 22.

FIG. 23 shows aberration diagrams of the thus-configured objective optical system of this Example. Although this Example has an extremely wide viewing angle, having an angle of view of 162°, it is possible to satisfactorily suppress aberrations over the entire image, thus exhibiting sufficiently high performance to be employed in a high-definition, high-pixel-count imaging device. In addition, the overall length is extremely short, being about 2.9 times the image height, and the outer diameters of constituent optical lenses can be made smaller, as opposed to being close to the image circle diameter, thus achieving a compact unit.

| Lens Data | | | | |
|---|---|---|---|---|
| Surface Number | r | d | ne | Vd |
| 1 | ∞ | 0.3729 | 1.51825 | 64.14 |
| 2 | ∞ | 0.0000 | 1.00000 | |
| 3(S) | ∞ | 0.0358 | 1.00000 | |
| 4 | −1.1970 | 0.4014 | 1.77621 | 49.60 |
| 5* | −0.5240 | 0.0224 | 1.00000 | |
| 6 | −2.4252 | 0.4107 | 1.69417 | 31.07 |
| 7* | −12.1151 | 0.0224 | 1.00000 | |
| 8 | ∞ | 0.1199 | 1.60697 | 20.00 |
| 9 | ∞ | 0.0000 | 9.3E+02 | −3.45 |
| 10* | −1.193E+04 | 0.2872 | 1.75538 | 33.00 |
| 11 | −5.5558 | 0.0224 | 1.00000 | |
| 12* | 5.2889 | 0.3268 | 1.53336 | 56.00 |
| 13 | 12.2175 | 0.2148 | 1.00000 | |
| 14 | ∞ | 0.4475 | 1.51825 | 64.14 |
| 15 | ∞ | 0.0746 | 1.00000 | |
| 16(IMG) | ∞ | | | |

Aspheric Surface Data

Surface 5

K = −0.8925  A4 = −6.0868E−02
A6 = 3.0355E+00

Surface 7

K = 225.3917  A4 = −5.8826E−01
A6 = 1.7596E−01  A8 = −2.8023E−01

Surface 10

K = −1.0000  A4 = 1.3256E−05
A6 = −2.3829E−05  A8 = 2.3364E−07

Surface 12

K = −0.7568  A4 = 3.2742E−02
A6 = −2.8077E−02  A8 = 1.3799E−02
A10 = 1.0475E−04

Miscellaneous data f = 1, Fno. = 7.13, 2ω = 161.6°
IH = 0.982, distance to object point 11.19

Note that, although the closely laminated diffractive optical element of this Example has the configuration shown in FIG. 33, the configuration shown in FIG. 34 can be employed without changes in the performance by slight alterations indicated by (A), (B), and (C) below:
(A) Change the surface spacing (d) of the 10th surface from 0.2872 to 0.04;
(B) Add a 10'-th surface, indicated below, between the 10th surface and the 11th surface:
r=∞, d=0.255, ne=1.81078, and vd=40.92; and
(C) Change the radius of curvature (r) of the 11th surface from −5.5558 to −5.964.

Example 2

Figure 24:
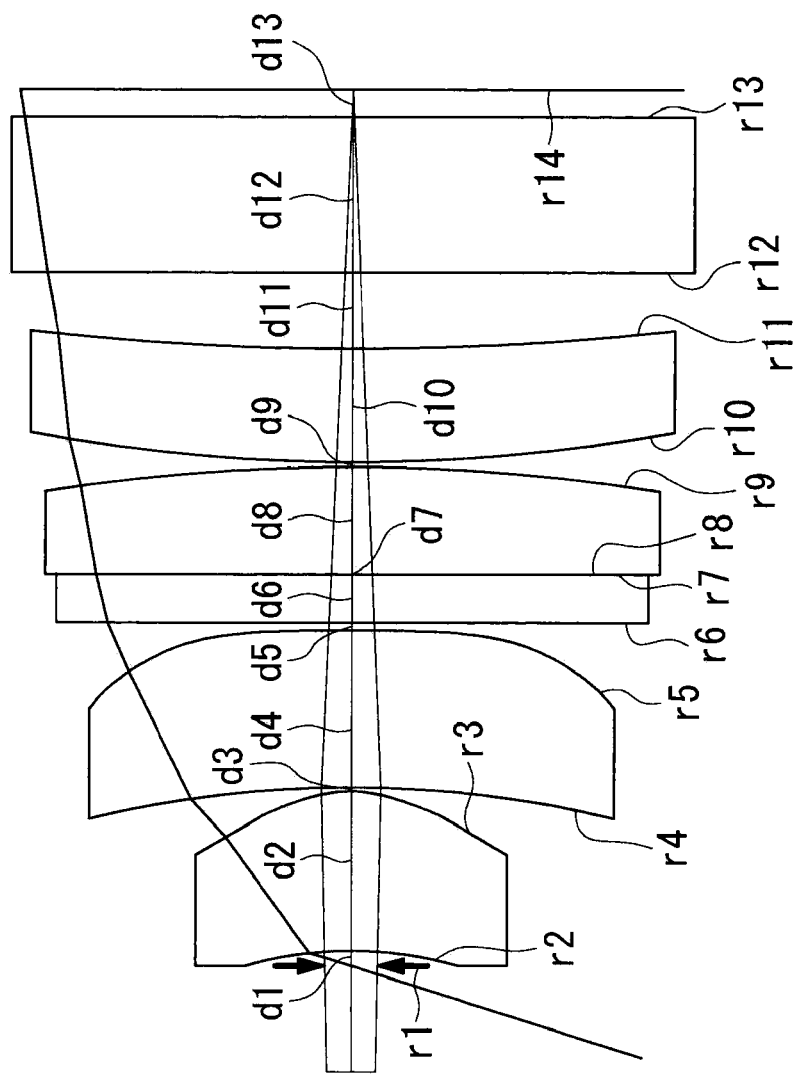
FIG. 24 is a cross-sectional view of a lens showing the overall configuration of the objective optical system according to Example 2 of the third embodiment.

As shown in FIG. 24 and the lens data below, an objective optical system according to Example 2 of the third embodiment is formed of, in order from the object side, an aperture stop, a first group formed of a positive meniscus lens whose convex surface faces the image side, a second group formed of a single lens, and a third group formed of a lens including diffractive optical elements and a lens in which the object-side surface thereof is an aspheric surface. The meniscus lens in the first group has an aspheric surface at the image-side surface where the curvature outward from the optical axis becomes gentle. The lens in the second group has an aspheric surface at the image-side surface.

The lens including the diffractive optical elements is a closely laminated diffractive optical element in which a material whose refractive index at the d line is 1.6 and whose Abbe number is 20 and a material whose refractive index at the d line is 1.74 and whose Abbe number is 33 are attached to each other. The representations of the surface shapes of the diffractive optical surfaces (7th surface and 8th surface) are given by the above-described ultra-high index method. Refractive indexes based on the ultra-high index method for the respective wavelengths at the 7th surface are as follows:
d line: 1001, C line: 1117.941,
e line: 930.3859,
F line: 828.3708, and
g line: 742.7625.

An actual diffractive optical element can be fabricated by determining the surface shape of a closely laminated diffractive optical element in which the phase calculated by the ultra-high index method can be achieved with the aspheric-surface shape of the 8th surface.

Figure 25:
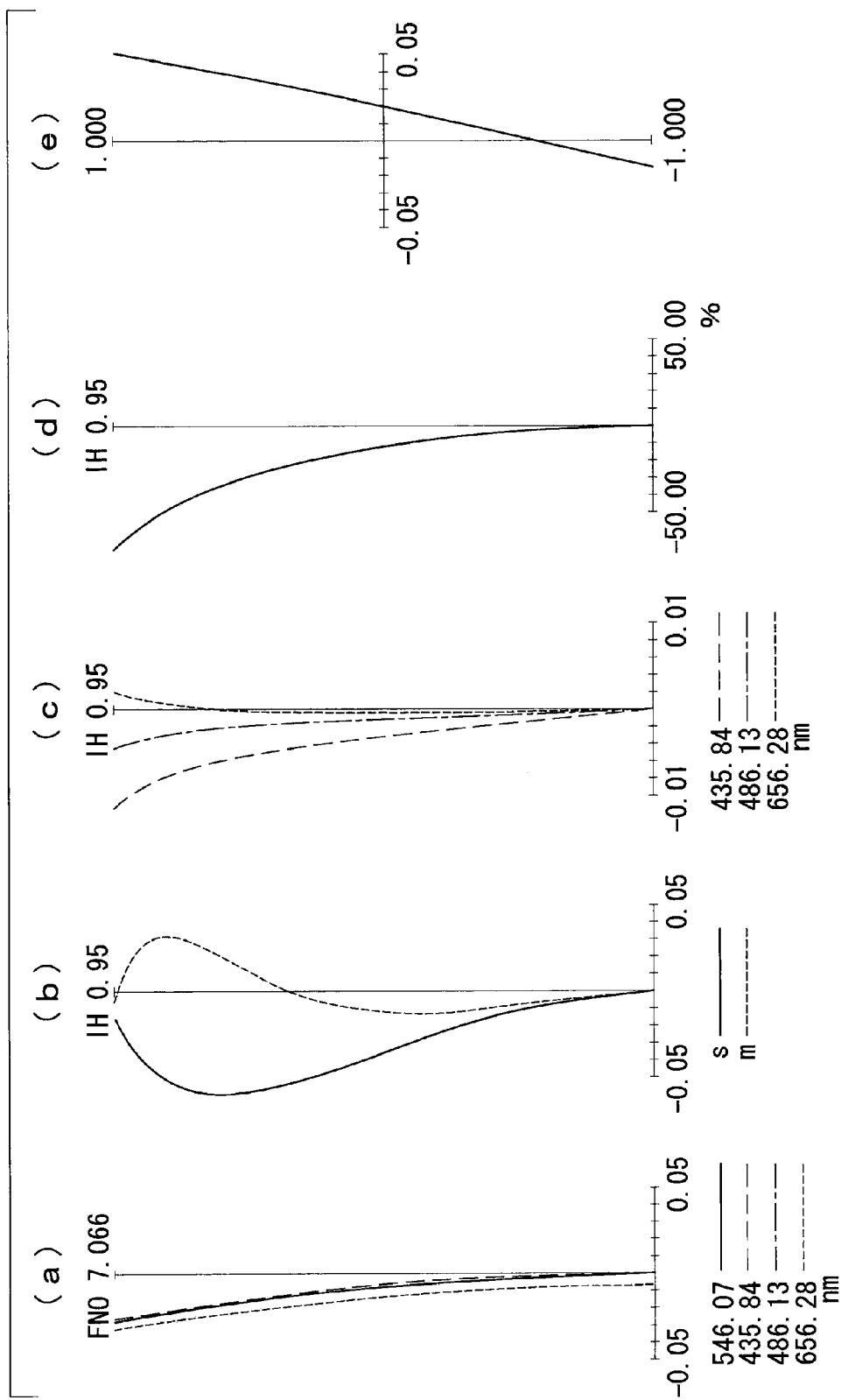
FIG. 25 is a diagram showing various types of aberration of the objective optical system in FIG. 24.

FIG. 25 shows aberration diagrams of the thus-configured objective optical system of this Example. Although this Example has an extremely wide viewing angle, having an angle of view of 145°, it is possible to satisfactorily suppress aberrations over the entire image, thus exhibiting sufficiently high performance to be employed in a high-definition, high-pixel-count imaging device. In addition, the overall length is extremely short, being about 3 times the image height, and the outer diameters of constituent optical lenses can be made smaller, as opposed to being close to the image circle diameter, thus achieving a compact unit.

Lens Data

| Surface Number | r | d | ne | Vd |
|---|---|---|---|---|
| 1(S) | ∞ | 0.0434 | 1.00000 | |
| 2 | −1.1326 | 0.4366 | 1.77621 | 49.60 |
| 3* | −0.5341 | 0.0217 | 1.00000 | |
| 4 | −3.2912 | 0.4372 | 1.69417 | 31.07 |
| 5* | −12.7510 | 0.0217 | 1.00000 | |
| 6 | ∞ | 0.1383 | 1.60697 | 20.00 |
| 7 | ∞ | 0.0000 | 9.3E+02 | −3.45 |
| 8* | −1.129E+04 | 0.2940 | 1.74530 | 33.00 |
| 9 | −6.1407 | 0.0217 | 1.00000 | |
| 10* | 6.8043 | 0.3083 | 1.53336 | 56.00 |
| 11 | 7.7203 | 0.2178 | 1.00000 | |
| 12 | ∞ | 0.4341 | 1.51825 | 64.14 |
| 13 | ∞ | 0.0724 | 1.00000 | |
| 14(IMG) | ∞ | | | |

Aspheric Surface Data

Surface 3

K = −0.8633    A4 = −1.5706E−01
A6 = 3.5599E+00

Surface 5

K = 225.3892    A4 = −6.1396E−01
A6 = 2.4624E−01    A8 = −3.4665E−01

Surface 8

K = −1.0000    A4 = 3.1680E−05
A6 = −2.7735E−05    A8 = 7.7059E−06

Surface 10

K = −0.7368    A4 = 2.9269E−02
A6 = −5.1281E−02    A8 = 5.0753E−02

Miscellaneous data f = 1, Fno. = 7.07, 2ω = 145.2°
IH = 0.952, distance to object point 10.8532

Note that, although the closely laminated diffractive optical element of this Example has the configuration shown in FIG. 33, the configuration shown in FIG. 34 can be employed without changes in the performance by slight alterations indicated by (A), (B), and (C) below:
(A) Change the surface spacing (d) of the 8th surface from 0.294 to 0.0461;
(B) Add an 8'-th surface, indicated below between the 8th surface and the 9th surface:
r=∞, d=0.257, ne=1.81078, and vd=40.92; and
(C) Change the radius of curvature (r) of the 9th surface from −6.1407 to −6.6810.

Example 3

Figure 26:
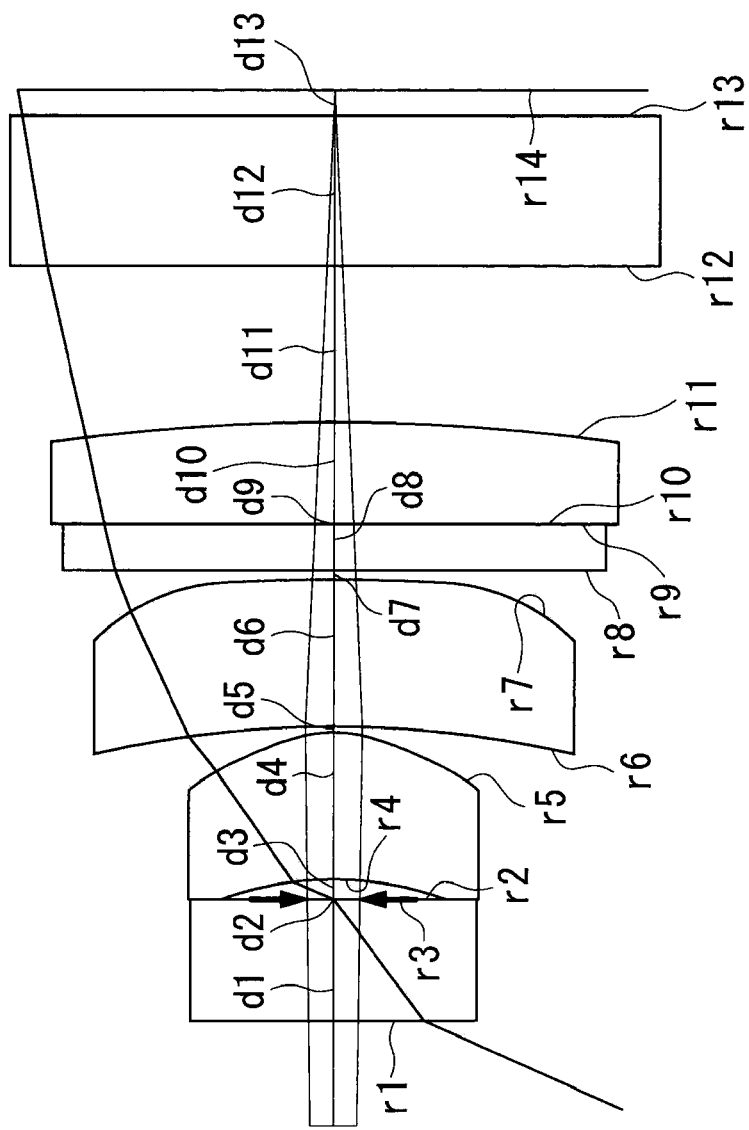
FIG. 26 is a cross-sectional view of a lens showing the overall configuration of the objective optical system according to Example 3 of the third embodiment.

As shown in FIG. 26 and the lens data below, an objective optical system according to Example 3 of the third embodiment is formed of, in order from the object side, a cover glass, an aperture stop, a first group formed of a positive meniscus lens whose convex surface faces the image side, a second group formed of a single lens, and a third group formed of a single lens including diffractive optical elements. The meniscus lens in the first group has an aspheric surface at the image-side surface where the curvature becomes outward from the optical axis gentle. The lens in the second group has an aspheric surface at the image-side surface.

The lens including the diffractive optical elements is a closely laminated type in which a material whose refractive index at the d line is 1.6 and whose Abbe number is 20 and a material whose refractive index at the d line is 1.75 and whose Abbe number is 33 are attached to each other. The surface shapes of the diffractive optical surfaces (9th surface and 10th surface) are represented based on the above-described ultra-high index method. Refractive indexes based on the ultra-high index method for the respective wavelengths at the 9th surface are as follows:
d line: 1001,
C line: 1117.941,
e line: 930.3859,
F line: 828.3708, and
g line: 742.7625.

An actual diffractive optical element can be fabricated by determining the surface shape of a closely laminated diffractive optical element in which the phase calculated by the ultra-high index method can be achieved with the aspheric-surface shape of the 10th surface.

Figure 27:
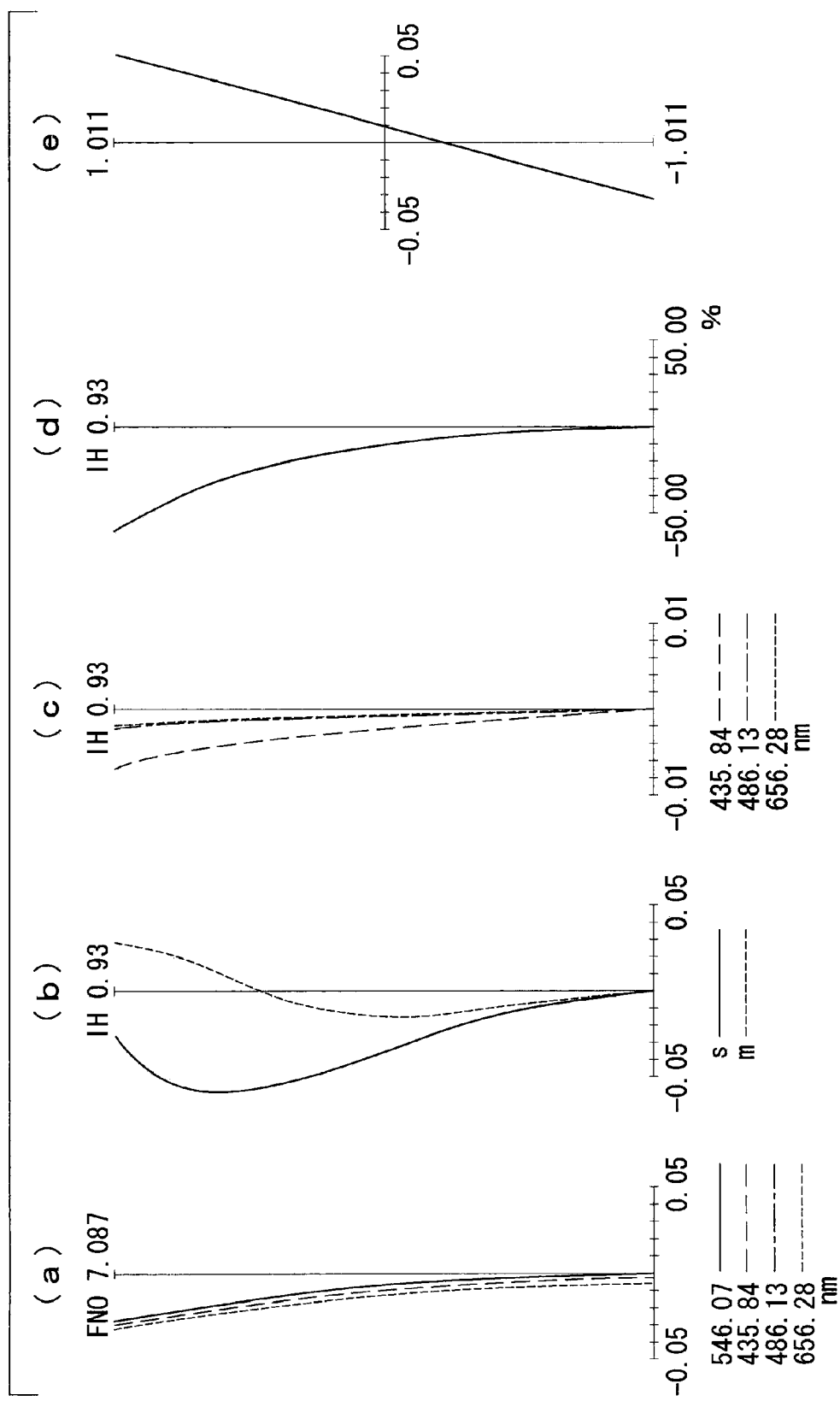
FIG. 27 is a diagram showing various types of aberration of the objective optical system in FIG. 26.

FIG. 27 shows aberration diagrams of the thus-configured objective optical system of this Example. Although this Example has a wide viewing angle, having an angle of view of 133°, it is possible to satisfactorily suppress aberrations over the entire image, thus exhibiting sufficiently high performance to be employed in a high-definition, high-pixel-count imaging device. In addition, the size thereof is extremely small, having an overall length of about 3.5 times the image height, and the outer diameters of constituent optical lenses can be made smaller, as opposed to being close to the image circle diameter, thus achieving a compact unit.

Lens Data

| Surface Number | r | d | ne | Vd |
|---|---|---|---|---|
| 1 | ∞ | 0.3528 | 1.51825 | 64.14 |
| 2 | ∞ | 0.0000 | 1.00000 | |
| 3(S) | ∞ | 0.0564 | 1.00000 | |
| 4 | −1.1085 | 0.4235 | 1.77621 | 49.60 |
| 5* | −0.5207 | 0.0212 | 1.00000 | |
| 6 | −3.1977 | 0.4249 | 1.69417 | 31.07 |
| 7* | −12.7612 | 0.0212 | 1.00000 | |
| 8 | ∞ | 0.1383 | 1.60697 | 20.00 |
| 9 | ∞ | 0.0000 | 9.3E+02 | −3.45 |
| 10* | −1.129E+04 | 0.2894 | 1.75538 | 33.00 |
| 11 | −6.1175 | 0.4534 | 1.00000 | |
| 12 | ∞ | 0.4233 | 1.51825 | 64.14 |
| 13 | ∞ | 0.0706 | 1.00000 | |
| 14(IMG) | ∞ | | | |

-continued

Aspheric Surface Data

Surface 5

| | |
|---|---|
| K = −0.8654 | A4 = −1.6366E−01 |
| A6 = 4.0512E+00 | |

Surface 7

| | |
|---|---|
| K = 225.3881 | A4 = −6.5486E−01 |
| A6 = 2.8787E−01 | A8 = −4.0320E−01 |

Surface 10

| | |
|---|---|
| K = −1.0000 | A4 = 1.9934E−05 |
| A6 = −3.1467E−05 | A8 = 6.8967E−06 |

Miscellaneous data f = 1, Fno. = 7.09, 2ω = 132.6°
IH = 0.928, distance to object point 10.58

Example 4

Figure 28:
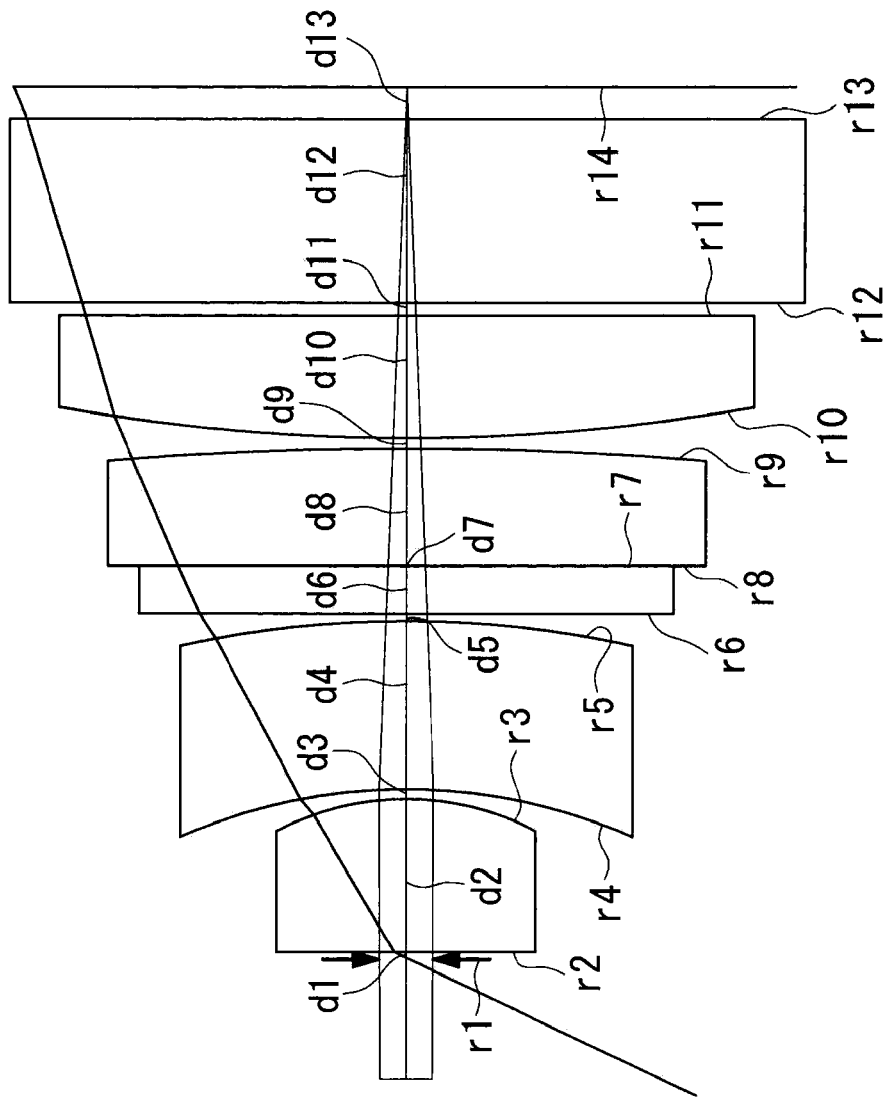
FIG. 28 is a cross-sectional view of a lens showing the overall configuration of the objective optical system according to Example 4 of the third embodiment.

As shown in FIG. 28 and the lens data below, an objective optical system according to Example 4 of the third embodiment is formed of, in order from the object side, an aperture stop, a first group formed of a positive plano-convex lens whose convex surface faces the image side, a second group formed of a single lens, and a third group formed of a lens including diffractive optical elements and a positive plano-convex lens whose convex surface faces the image side. The meniscus lens in the first group has an aspheric surface at the image-side surface where the curvature outward from the optical axis becomes gentle. The lens in the second group has an aspheric surface at the image-side surface.

The diffractive optical element of the third group is a closely laminated in which a material whose refractive index at the d line is 1.6 and whose Abbe number is 20 and a material whose refractive index at the d line is 1.75 and whose Abbe number is 33 are attached to each other. The surface shapes of the diffractive optical surfaces (7th surface and 8th surface) are represented based on the above-described ultra-high index method. Refractive indexes based on the ultra-high index method at the 7th surface are as follows:

d line: 1001,

C line: 1117.941, e line: 930.3859,

F line: 828.3708, and g line: 742.7625.

An actual diffractive optical element can be fabricated by determining the surface shape of a closely laminated diffractive optical element in which the phase calculated by the ultra-high index method can be achieved with the aspheric-surface shape of the 8th surface.

Figure 29:
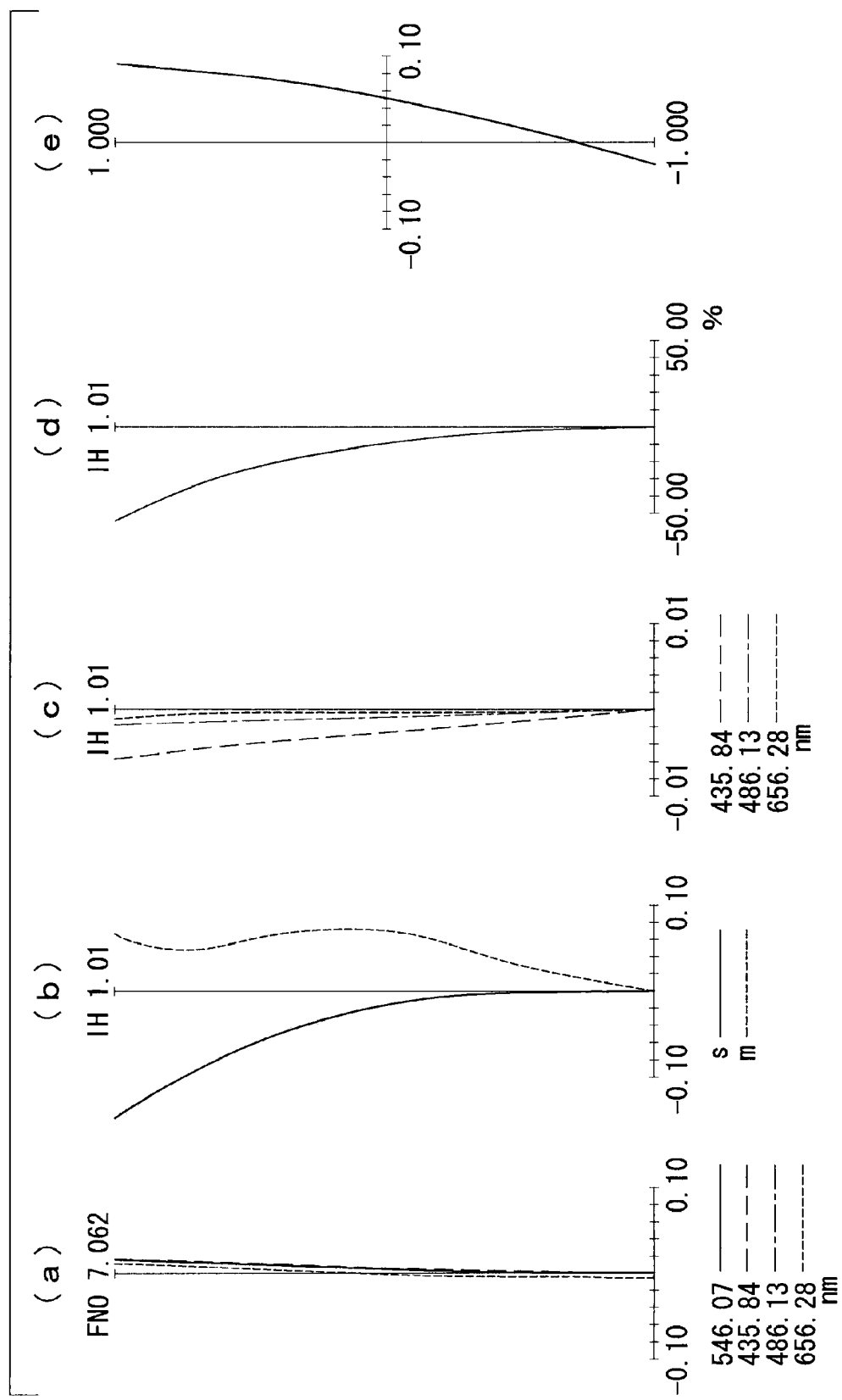
FIG. 29 is a diagram showing various types of aberration of the objective optical system in FIG. 28.

FIG. 29 shows aberration diagrams of the thus-configured objective optical system of this Example. Although this Example has a wide viewing angle, having an angle of view of 130°, it is possible to satisfactorily suppress aberrations over the entire image, thus exhibiting sufficiently high performance to be employed in a high-definition, high-pixel-count imaging device. In addition, the size thereof is extremely small, having an overall length of about 3 times the image height, and the outer diameters of constituent optical lenses can be made smaller, as opposed to being close to the image circle diameter, thus achieving a compact unit.

Lens Data

| Surface Number | r | d | ne | Vd |
|---|---|---|---|---|
| 1(S) | ∞ | 0.0154 | 1.00000 | |
| 2 | ∞ | 0.3848 | 1.77621 | 49.60 |
| 3* | −0.6329 | 0.0231 | 1.00000 | |
| 4 | −1.5531 | 0.4233 | 1.69417 | 31.07 |
| 5* | −10.2102 | 0.0231 | 1.00000 | |
| 6 | ∞ | 0.1231 | 1.60697 | 20.00 |
| 7 | ∞ | 0.0000 | 9.3E+02 | −3.45 |
| 8* | −1.231E+04 | 0.2925 | 1.74530 | 33.00 |
| 9 | −8.1071 | 0.0231 | 1.00000 | |
| 10 | 5.2272 | 0.3079 | 1.53336 | 56.00 |
| 11 | ∞ | 0.0279 | 1.00000 | |
| 12 | ∞ | 0.4618 | 1.51825 | 64.14 |
| 13 | ∞ | 0.0770 | 1.00000 | |
| 14(IMG) | ∞ | | | |

Aspheric Surface Data

Surface 3

| | |
|---|---|
| K = −1.5979 | A4 = 1.2370E+00 |
| A6 = −5.7116E+00 | |

Surface 5

| | |
|---|---|
| K = 224.9839 | A4 = −3.8940E−01 |
| A6 = −2.5397E−02 | A8 = 7.2292E−01 |

Surface 8

| | |
|---|---|
| K = −1.0000 | A4 = 1.2064E−05 |
| A6 = −2.0367E−05 | A8 = 1.8755E−07 |

Miscellaneous data f = 1, Fno. = 7.06, 2ω = 130.3°
IH = 1.013, distance to object point 11.545

Table 3 shows values of Conditional Expressions (12) to (15) for the objective optical systems according to Examples 1 to 4 of the third embodiment described above.

TABLE 3

| Conditional Expression | Example 1 | Example 2 | Example 3 | Example 4 |
|---|---|---|---|---|
| (1) f/f2 | −0.225 | −0.154 | −0.160 | −0.371 |
| (2) f/f3 | 0.271 | 0.215 | 0.204 | 0.268 |
| (3) f/f34 | 0.058 | 0.010 | — | 0.102 |
| (4) f/f1 | 1.050 | 1.013 | 1.040 | 1.227 |

{Additional Remarks}

Note that inventions having the following configurations can be derived from the above-described Examples of the third embodiment.

{Additional Item 1'}

An objective optical system provided with, in order from the object side, an aperture stop, a positive first group, a second group, and a positive third group, wherein the first group is formed of a meniscus lens whose convex surface faces the image side, the second group is formed of a single lens, the third group is formed of a single lens including a close-contact multilayered diffractive optical element, and Conditional Expressions (12) and (13) below are also satisfied:

$$-0.4 \leq f/f2 \leq -0.05, \text{ and} \tag{12}$$

$$0.1 \leq f/f3 < 0.4, \tag{13}$$

where f2 is the focal length of the second group, f3 is the focal length of the third group, and f is the focal length of the entire system.

{Additional Item 2'}

An objective optical system according to Additional Item 1', satisfying Conditional Expression (15) below:

$$0.9 \leq f/f1 \leq 1.4, \quad (15)$$

where f1 is the focal length of the first group.

{Additional Item 3'}

An optical system according to Additional Item 2', wherein the lens in the second group has an aspheric surface at the image-side surface thereof.

{Additional Item 4'}

An objective optical system provided with, in order from the object side, an aperture stop, a positive first group, a second group, and a positive third group, wherein the first group is formed of a single meniscus lens or plano-convex lens, whose convex surface faces the image side, the second group is formed of a single lens, the third group is formed of a close-contact multilayered diffractive optical element and another lens, and Conditional Expressions (12) to (14) below are also satisfied:

$$-0.4 \leq f/f2 \leq -0.05, \quad (12)$$

$$0.1 \leq f/f3 \leq 0.4, \text{ and} \quad (13)$$

$$0.001 \leq |f/f34| \leq 0.2, \quad (14)$$

where f2 is the focal length of the second group, f3 is the focal length of the third group, f34 is the focal length of the another lens, and f is the focal length of the entire system.

{Additional Item 5'}

An objective optical system according to Additional Item 4', satisfying Conditional Expression (15) below:

$$0.9 \leq f/f1 \leq 1.4, \quad (15)$$

where f1 is the focal length of the first group.

{Additional Item 6'}

An objective optical system according to Additional Item 5', wherein the lens in the second group has an aspheric surface at the image-side surface thereof.

REFERENCE SIGNS LIST

1, 1', 1'' objective optical system
G1, G1', G1'' first group
G2, G2', G2'' second group
G3, Gs3', G3'' third group
G4' fourth group
L1 positive lens
L1', L1'', L2', L2'', L4, L4', L4'' meniscus lens
L2 negative lens
L3 positive meniscus lens
L3', LC cemented lens
L3'' lens including diffractive optical element
L31' meniscus lens (negative lens)
L32' double-convex lens (positive lens)
L31'', L32'' diffractive optical element
31a, 32a diffractive optical surface
F1, F2 flat-parallel plate
IMG image plane
S aperture stop

The invention claimed is:

1. An objective optical system comprising, in order from an object side:
   an aperture stop;
   a positive first group;
   a second group; a positive third group; and
   a fourth group,
   wherein the first group is formed of a single meniscus lens or plano-convex lens, whose convex surface faces an image side,
   the second group is formed of a single lens,
   the third group is formed of a cemented lens consisting of a positive lens and a negative lens,
   the fourth group is formed of a single lens, and
   Conditional Expressions (7) and (8) below are satisfied:

$$-0.5 < f/f4 < -0.001, \text{ and} \quad (7)$$

$$0.1 \leq |f4/f2| \leq 5, \quad (8)$$

where f is a focal length of an entire system,
f4 is a focal length of the fourth group, and
f2 is a focal length of the second group.

2. The objective optical system according to claim 1, wherein Conditional Expression (9) below is satisfied:

$$0.3 < f/f3 < 0.8, \quad (9)$$

where f3 is a focal length of the third group.

3. The objective optical system according to claim 2, wherein Conditional Expression (10) below is satisfied:

$$0.15 < f/f1 < 1.1, \quad (10)$$

where f1 is a focal length of the first group.

4. The objective optical system according to claim 3, wherein the first group satisfies Conditional Expression (11) below:

$$1 \leq |(C1+C2)/(C1-C2)| < 40, \quad (11)$$

where C1 is a curvature of an object-side surface of the first group, and
C2 is a curvature of an image-side surface of the first group.

* * * * *